(12) United States Patent
Puzey

(10) Patent No.: US 7,894,057 B2
(45) Date of Patent: *Feb. 22, 2011

(54) METHODS OF ANALYZING SAMPLES USING BROADBAND LASER LIGHT

(75) Inventor: Kenneth A. Puzey, Essex Junction, VT (US)

(73) Assignee: QuantaSpec, Inc., Burlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/578,629

(22) Filed: Oct. 14, 2009

(65) Prior Publication Data

US 2010/0045977 A1     Feb. 25, 2010

Related U.S. Application Data

(63) Continuation of application No. 11/087,939, filed on Mar. 22, 2005, now Pat. No. 7,623,234.

(60) Provisional application No. 60/555,166, filed on Mar. 22, 2004, provisional application No. 60/599,692, filed on Aug. 6, 2004.

(51) Int. Cl.
    *G01J 3/28*     (2006.01)

(52) U.S. Cl. ..................................... 356/326

(58) Field of Classification Search ................ 356/326, 356/335, 317

See application file for complete search history.

(56) References Cited

U.S. PATENT DOCUMENTS

| | | |
|---|---|---|
| 4,054,389 A | 10/1977 | Owen |
| 4,149,805 A | 4/1979 | Chew, III |
| 4,269,481 A | 5/1981 | Yeh et al. |
| 4,508,964 A | 4/1985 | Gunning et al. |
| 5,250,810 A | 10/1993 | Geiger |
| 5,373,160 A | 12/1994 | Taylor |
| 6,278,522 B1 | 8/2001 | Lepper et al. |
| 6,421,166 B1 | 7/2002 | Velsko et al. |
| 6,586,193 B2 | 7/2003 | Yguerabide et al. |
| 6,593,582 B2 | 7/2003 | Lee et al. |
| 6,608,677 B1 | 8/2003 | Ray et al. |
| 6,700,690 B1 | 3/2004 | Buchsbaum et al. |

(Continued)

OTHER PUBLICATIONS

Sub-part-per-billion detection of nitric oxide in air using a thermoelectrically cooled mid-infrared quantum cascade laser spectrometer; D.D. Nelson, J.H. Shorter, J.B. McManus, M.S. Zahniser; Applied Physics B—Lasers and Optics 75, 343-350 (2002.

(Continued)

*Primary Examiner*—Tarifur Chowdhury
*Assistant Examiner*—Jonathan M Hansen
(74) *Attorney, Agent, or Firm*—Downs Rachlin Martin PLLC

(57) ABSTRACT

Broadband light, for example, from a Fabry-Perot quantum cascade laser, is shone onto a sample, and spectral data concerning the broadband light reflected from the sample is collected. The spectral data is analyzed to determine information about one or more substances in the sample. For example, if the sample contains micro-organisms, such as bacteria or fungus, the biological classification(s) (e.g., species) of the micro-organisms can be determined from the spectral data. As another example, if the sample contains virus, the biological classification(s) (e.g., species) of the virus(es) can be determined from the spectral data. As yet another example, if the sample contains particles, size, location and velocity can be determined from the spectral data.

17 Claims, 13 Drawing Sheets

U.S. PATENT DOCUMENTS

| | | | |
|---|---|---|---|
| 7,010,010 B2 * | 3/2006 | Capasso et al. | 372/45.01 |
| 2001/0025927 A1 | 10/2001 | Ankerhold | |
| 2002/0138210 A1 * | 9/2002 | Wilkes et al. | 702/28 |
| 2002/0158202 A1 | 10/2002 | Webber et al. | |
| 2003/0030801 A1 | 2/2003 | Levenson et al. | |
| 2003/0218750 A1 | 11/2003 | Friberg et al. | |
| 2003/0223063 A1 | 12/2003 | Hill et al. | |
| 2004/0024540 A1 | 2/2004 | Bove et al. | |
| 2004/0211906 A1 | 10/2004 | Lendl | |
| 2004/0252300 A1 | 12/2004 | Slater | |

OTHER PUBLICATIONS

Thermoelectrically cooled quantum cascade laser based sensor for continuous monitoring of ambient atmospheric CO; A.A. Kosterev, F.K. Tittel, R. Kohler, C. Gmachl, F. Capasso, D.L. Sivco, A.Y.Cho, S. Wehe and M. Allen; Optical Society of America; Applied Optics, vol. 41, No. 6, 2002.

Quantitative Gas Sensing by Backscatter-Absorption Measurements of a Pseudo-Random Code Modulated $\lambda \sim 8$ μm Quantum Cascade Laser; C.M. Gittins, E.T. Wetjen, C. Gmachl, F. Capasso, A.L. Hutchinson, D.L. Sivco, J.N. Baillargeon, A.Y. Cho; Optics Letters 25(16), 1162-1164 (Aug. 15, 2000) Optical Society of America.

Measurement of nitric oxide with an antimonide diode laser; Daniel B. Oh and Alan C. Stanton; Applied Optics, vol. 36, No. 15, pp. 3294-3297, May 2, 1997.

Blaser et al., "High power and single frequency quantum cascade lasers for gas sensing" Jan. 2004, Proceedings of SPIE vol. 5240, pp. 137-141.

First Office Action dated Nov. 17, 2006, with regard to related U.S. Appl. No. 11/087,939, filed Mar. 22, 2005, Puzey.

Amendment and Response to First Office Action dated Mar. 19, 2007, with regard to related U.S. Appl. No. 11/087,939, filed Mar. 22, 2005, Puzey.

Kosterev, Anatoliy A. et al., "Chemical Sensors Based on Quantum Cascade Lasers" IEEE Journal of Quantum Electronics, vol. 38, No. 6, Jun. 2002, pp. 528-591.

Final Office Action dated Jun. 5, 2007, with regard to related U.S. Appl. No. 11/087,939, filed Mar. 22, 2005, Puzey.

Preliminary Amendment accompanying first RCE dated Dec. 3, 2007, with regard to related U.S. Appl. No. 11/087,939, filed Mar. 22, 2005, Puzey.

Supplemental Preliminary Amendment dated Dec. 6, 2007, with regard to related U.S. Appl. No. 11/087,939, filed Mar. 22, 2005, Puzey.

Clair Gmachl et al., "Minimal Group Refractive Index Dispersion and Gain Evolution in Ultra-Broadband Quantum Cascade Laser" Dec. 2002, IEEE Photonics Technology letters, vol. 14.

Alexander Soibel et al., "Active Mode Locking of Broadband Quantum Cascade Lasers" Jul. 2004, IEEE Journal of Quantum Electronics, vol. 40.

First Office Action after RCE dated Dec. 26, 2007, with regard to related U.S. Appl. No. 11/087,939, filed Mar. 22, 2005, Puzey.

Response to First Office Action after RCE dated Jun. 26, 2008, with regard to related U.S. Appl. No. 11/087,939, filed Mar. 22, 2005, Puzey.

Second Office Action after RCE dated Oct. 14, 2008, with regard to related U.S. Appl. No. 11/087,939, filed Mar. 22, 2005, Puzey.

Response to Second Office Action after RCE dated Apr. 14, 2009, with regard to related U.S. Appl. No. 11/087,939, filed Mar. 22, 2005, Puzey.

Notice of Allowance dated Jul. 29, 2009, with regard to related U.S. Appl. No. 11/087,939, filed Mar. 22, 2005, Puzey.

* cited by examiner

US 7,894,057 B2

METHODS OF ANALYZING SAMPLES USING BROADBAND LASER LIGHT

RELATED APPLICATION DATA

This application is a continuation of U.S. patent application Ser. No. 11/087,939, filed Mar. 22, 2005, and titled "System And Method For Detecting And Identifying An Analyte" (now U.S. Pat. No. 7,623,234), which claims the benefit of priority of U.S. Provisional Patent Application Ser. No. 60/555,166, filed Mar. 22, 2004, and titled "Method And Means For Remote Particle Sensing" and U.S. Provisional Patent Application Ser. No. 60/599,692, filed Aug. 6, 2004, and titled "Method And Apparatus For Remote Sensing." Each of the foregoing applications is incorporated by reference herein in its entirety.

FIELD OF THE INVENTION

The present invention generally relates to the field of automated testing. In particular, the present invention is directed to methods of analyzing samples using broadband laser light.

BACKGROUND

The ability to sense and identify matter using automated equipment has been known for many years and is important to the general field of testing that has application in the physical sciences and across a broad spectrum of modern pursuits that rely on the physical sciences, including manufacturing, medicine, government regulation, e.g., regulation of pollutants, air quality, etc., detection of harmful substances, e.g., substances such as anthrax, nerve agents and other agents used in biological and chemical weapons, and analytes that are out-gassed or otherwise given off by harmful substances, e.g., explosives such as trinitrotoluene (TNT) and cyclotrimethylene trinitramine (a.k.a. RDX, cyclonite or hexogen), among many others. Conventional sensing and identifying methods that have been used to detect one or more of the analytes mentioned above and/or other analytes include ion mobility spectrometry, flame photometry, mass spectrometry, electrochemistry, detection paper methods, surface acoustic wave methods, laser-induced breakdown spectroscopy, photo ionization detection, gas chromatography and cavity-ring-down spectroscopy.

The detecting methods just mentioned are generally equipment-centric, i.e., a sample believed to contain the analyte under consideration must be captured and placed either within, or at least in close proximity to, the equipment that either performs or is used in performing the corresponding method. However, equipment-centric methods are generally not suited to a number of applications, especially applications where it is, among other things: (1) difficult or impractical to place testing equipment at the location of the analyte to be tested; (2) difficult or impractical to retrieve a sample of the analyte from a particular location and test the sample at a location away from the location where the sample was obtained and/or (3) dangerous to place testing equipment at, and retrieve a sample from, the location where the analyte may be present. In these applications it is desirable to utilize a remote sensing and identifying method.

Important attributes of the equipment, i.e., "sensor," used to perform a detecting method, either equipment-centric or remote, include selectivity, sensitivity and response time. An additional attribute that can be important for a remote-detecting sensor is range. Generally, "selectivity" refers to the ability of a sensor to discriminate between an analyte of interest and one or more interferents. For example, organo-phosphate insecticides, such as malathion, parathion, etc., are common interferents in detecting certain toxic nerve agents, e.g., GA (Tabun), GB (Sarin), GD (Soman), GF, VX, etc. As another example, *Bacillus subtilis* is a common interferent in detecting *Bacillus anthracis* (anthrax). "Sensitivity" generally refers to the ability of the sensor to detect low concentrations levels of the analyte of interest and is often measured in particles per liter (volume concentration) or particles per square meter (surface concentration). In the case of microorganisms, the appropriate concentration units may be colony forming units (CFUs) per liter (volume concentration) or CFUs per square meter (area concentration). Response time generally refers to the elapsed time it takes the sensor to detect and identify the analyte of interest as measured from the time the sensor is either triggered (in the case where the sensor is triggerable) or the analyte first becomes available for detection (in the case where the sensor is continuously seeking to detect a particular analyte). For many conventional sensors, response time increases with decreasing concentrations. Range generally refers to the maximum physical distance between the sensor and the analyte at which a particular concentration of the analyte can be detected. For sensors that are used to quantify the amount of analyte present, the dynamic range is also an important capability. Dynamic range refers to the minimum and maximum amount of analyte that can be quantified.

Examples of conventional remote detectors include Raman spectroscopy, photoluminescence, Fourier transform infrared (FTIR) detectors, forward looking infrared (FLIR) detectors and differential absorption light detection and ranging (LiDAR) (DIAL) detectors. However, conventional embodiments of these detectors have one or more drawbacks or undesirable limitations under certain circumstances.

For example, Raman based sensors illuminate samples with ultraviolet light and look for a Raman shift in the reflected signal. Unfortunately, the atmosphere strongly absorbs infrared light severely limiting the range and sensitivity of such systems. Furthermore, the Raman shift is a very inefficient process and, therefore, has a severely limited sensitivity. Photoluminescence illuminates a sample with ultraviolet light and looks for re-radiated IR photons. Only a limited number of chemical compounds such as aromatic hydrocarbons will photoluminesce. Therefore this approach is limited in the type of analytes it can detect. In addition, it suffers from drawbacks in sensitivity and range because the ultraviolet light required is absorbed strongly by the atmosphere. Furthermore, photoluminescence is not very selective.

FTIR sensors suffer from several operational drawbacks when attempting to use such devices as remote sensors. First, FTIR sensors rely on an interferometer that generally requires the instrument to be stationary while acquiring measurement data. Second, it is necessary to record a background reference that is free of the analyte of interest prior to detecting that analyte. This limits the operational flexibility and mobility of FTIR sensors. For example, when moving to a new location for detecting analyte in a new region, it is essential to use other detectors to ensure that the analyte of interest is not present in the new region before recording background spectra. Once a background reference has been obtained, the FTIR sensor will then detect if the analyte of interest enters the new region. Moving an FTIR sensor to yet another location requires that the steps for obtaining a proper background reference be repeated. Therefore, FTIR sensors are not suitable for detection of analytes on the move. In addition to these flexibility and mobility issues, the infrared light sources used in FTIR detectors typically lack spectral intensity, thereby limiting the sensitivity, and range of the sensors.

A FLIR sensor uses a FLIR detector array and a set of filters that allows a user to visually detect the presence of certain chemical analytes. The sensitivity and selectivity of FLIR detection are highly dependent on the user's ability to interpret contrasts created in the visual field by looking at a scene using various different filters. FLIR detection is generally limited to sensing and identifying simple analytes, such as certain chemicals, and is unsuitable for identifying microorganisms, such as bacteria. Furthermore, this form of sensor is not easily automated and therefore requires a trained and vigilant person to perform detection.

Many DIAL sensors use carbon dioxide lasers to identify chemical analytes. One drawback of carbon dioxide lasers is that they are limited to using the spectral lines available from the carbon dioxide gain media. This limited wavelength selection limits the sensitivity and selectivity of prior art DIAL sensors. For example, FIG. 1A shows spectral absorption curves of the chemical warfare agents DMMP, GA, GB, GD, DPMP and TEP, along with the laser lines L that can be produced by a carbon dioxide laser. Note that the best line $L_1$ available from a carbon dioxide laser for detecting agents GB and GD is at only half of the absorption peak of agent GB, limiting sensitivity to half of what would otherwise be achievable. In addition, there is no carbon dioxide laser line L available at the primary absorption peak $P_{GA}$ of agent GA. Furthermore, carbon dioxide laser based DIAL sensors lack the ability to generate and detect the broad spectral information required to identify micro-organisms, such as bacteria. Furthermore, these carbon dioxide laser systems are large, heavy, and require a large amount of power to operate.

In addition to the previous limitations, prior art carbon dioxide laser DIAL systems are limited in the pulses per second they can produce. Typical systems produce one set of multi-wavelength pulses per second. Since the signal-to-noise (S/N) ratio of a system can be improved by co-adding multiple measurements, the number of measurements that can be made per second is an important determinant in the response time/sensitivity trade-off of a sensor. The S/N ratio of a system improves with the square root of the number of co-added measurements. Therefore, if two systems have equal S/N ratios per measurement and system A performs one measurement per second and system B performs a million measurements per second, then system B can improve its sensitivity by a factor of 1,000 over system A without any increase in response time. Alternatively, System B can achieve the same sensitivity and reduce system response time by a factor of 1 million.

More recently, a DIAL sensor was developed that uses a quantum cascade (QC) laser to provide spectral information. Nelson, Shorter, Micmanus and Zahniser report using a QC-laser-based DIAL sensor to perform sub-part-per-billion detection of trace gases in their paper, "Sub-part-per-billion detection of nitric oxide in air using a thermoelectrically cooled mid-infrared quantum cascade laser spectrometer," Applied Physics B Vol. 75, 2002, pp. 345-50, which is incorporated herein by reference in its entirety. In the Nelson et al. approach, the optical output frequency of the QC laser is swept with a bias ramp applied through a bias tee in a pulsed manner. The output of the QC laser is passed into a multi-pass gas cell that contains a sample either suspected or known to contain a particular chemical analyte. A broadband infrared detector is used to detect the output of the gas cell.

The Nelson et al. sensor suffers from several drawbacks and limitations. First, the spectral resolution of the sensor is limited by the relatively wide spectral pulses of the QC laser, thereby causing reduced selectivity. Second, these spectrally wide pulses can result in reduced sensitivity if the laser linewidth is wider than the spectral absorption feature to be detected. Third, in order to maintain as narrow a spectral pulse width as possible (and, thus, maximizing spectral resolution) the QC laser is operated at low power, i.e., near its operating threshold, thereby limiting both range and sensitivity. Fourth, the sensor is prone to saturation because the laser is operated at low power. In other words, if the sensor is used to quantify the amount of analyte present it is limited in the maximum concentration it can measure by the power of the laser pulse used. Fifth, the Nelson et al. method collects the spectrum of the sampled gas sequentially over a series of laser pulses, thereby increasing detection, and response, time.

FIG. 1B shows a plot 10 of a series of three pulses 12A, 12B, 12C of the pulsed laser output power as a function of wavelength at three different times, $t_1$, $t_2$, $t_3$, as used in the Nelson et al. method. Again, it is noted that the output power of the QC laser is kept close to the operating threshold of the laser so as to minimize the spectral width and maximize the spectral resolution. The output wavelength of the QC laser is shifted by applying a voltage ramp through a bias tee. FIG. 1C is an exemplary plot 16 of a spectral absorption profile 18 of the analyte that is desired to be detected using the laser output shown in FIG. 1B. Note the presence of a "valley" feature 22 of profile 18 that forms two "peak" features 24A, 24B. FIG. 1D is a plot 28 of the pulsed laser output of FIG. 1B as detected over a period that includes times $t_1$, $t_2$, $t_3$ after passing through the gas with absorption characteristics shown in FIG. 1C by the Nelson et al. broadband infrared sensor. FIG. 1D clearly shows that there is significant "blurring" of features 22, 24A, 24B of plot of FIG. 1C that has completely masked these features. Generally, this is so because of the scanning of the absorption band with pulses of FIG. 1B that have widths W that are wider than any of individual features of absorption profile 18 of FIG. 1C. Mathematically, the broadband nature of pulses 12A-C is a power integrator, with the detected power of FIG. 1C being a convolution of the pulses of FIG. 1B with the absorption profile 18 of FIG. 1C. This example illustrates the drawbacks in sensitivity, selectivity, and dynamic range of Nelson et al.

SUMMARY

In one embodiment, a method of identifying a biological classification of virus present in a sample, the method including: illuminating the sample with a spectral energy band across at least a portion of the characteristic absorption band of the analyte using an illuminator consisting essentially of one or more broadband quantum cascade lasers so as to provide the spectral energy band across a broadband of wavelengths; collecting spectral data regarding the sample using a detector; and determining a biological classification of the virus as a function of the spectral data.

In another embodiment, a method of identifying a biological classification of micro-organisms present in a sample, the method including: illuminating the sample with a spectral energy band across at least a portion of the characteristic absorption band of the analyte using an illuminator consisting essentially of one or more broadband quantum cascade lasers so as to provide the spectral energy band across a broadband of wavelengths; simultaneously collecting spectral data regarding the sample using a detector; and determining the biological classification of the micro-organisms as a function of the spectral data.

In yet another embodiment a method including: illuminating a plurality of particles, from a standoff distance, with a spectral energy band across at least a portion of the characteristic non-absorption band of the plurality of particles using an illuminator consisting essentially of one or more broadband quantum cascade lasers so as to provide the spectral energy band across a broadband of wavelengths; collecting spectral data regarding the plurality of particles using a detector; and determining sizes of the particles based on the spectral data.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION

Figure 2:
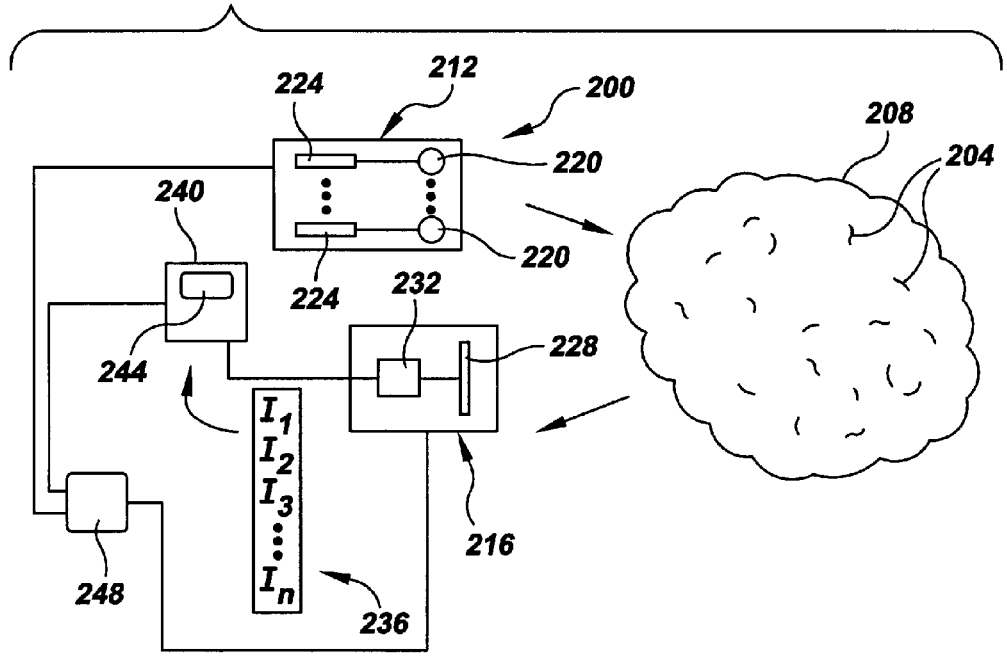
FIG. 2 is a high-level schematic diagram of an analyte sensor of the present invention.

Referring now to FIG. 2, there is shown in accordance with the present invention an analyte detecting and identifying system, or "sensor," which is generally denoted by the numeral 200. In general, sensor 200 is operatively configured to detect the presence of and/or identify one or more analytes 204 of interest in a sample region 208 by directing spectral energy into the region and sensing this energy, or lack thereof, after it passes out of the region. As is well known, due to their chemical structure different analytes have different spectral absorption characteristics across various wavelengths, much like different human finger prints have different patterns of ridges and valleys. These spectral absorption characteristics, being unique to the analyte, allow analytes to be detected and identified.

Identifying an analyte, such as analyte 204, generally involves chemical identification and/or biological identification. In chemical identification, an analyte may be identified according to its chemical composition. Analytes of interest relative to chemical identification may include chemical warfare agents, chemical agent precursors, chemical agent by-products, chemical agent intermediates, toxic industrial chemicals, pollutants, explosives, biological toxins, prions and impurities, among many others. In biological identification, an analyte may be identified according to its taxonomic classification, e.g., by its genus/species classification. The identification of biological organisms is also performed by analyzing their spectral signature. Analytes of interest relative to biological identification may include bacteria, viruses, Rickettsiae, bacterial spores, biotoxins, and fungal spores, among many others. Those skilled in the art will readily appreciate that the foregoing examples of analytes are merely illustrative and that it would be impractical to list all analytes that may be detected and/or identified in accordance with the present invention. Such skilled artisans will understand that virtually any analyte having unique spectral absorption characteristics may be detected and identified using a sensor and method of the present invention.

In addition to being able to detect and/or identify one or more analytes, a sensor of the present invention, e.g., sensor 200, may also be operatively configured to analyze one or more of various properties of the detected/identified analyte. For examples properties that can be analyzed include, but are not limited to, concentration level, range, concentration level as a function of range, location, particle size, particle size distribution, speed and velocity. A sensor of the present invention may then use one or more of these analyzed properties to creates maps of the identified analyte and the analyzed property(ies). These analysis and mapping features are described below in detail.

Referring still to FIG. 2, sensor 200 may comprise an illuminator 212 for illuminating at least a portion of sample region 208 with light across one or more spectral energy bands of interest and a receiver 216 for sensing at least a portion of the spectral energy band of this light. In general, illuminator 212 illuminates sample region 208 with relatively intense light across one or more pre-selected absorption bands of interest that are each selected based upon the spectral characteristics of the one or more analytes 204 of interest within the region in which detection is desired. Generally, each absorption band of interest is a range of wavelengths in which the absorption characteristics of analyte(s) 204 of interest are desired to be measured in order to detect and/or identify the analyte(s).

Receiver 216 then receives the portion of this light from illuminator 212 that exits sample region 208 after the light has interacted with the contents of the region, including analyte(s) 204 that may or may not be present within the region. As discussed in more detail below, depending upon the location of receiver 216 relative to illuminator and the character and location of sample region 208 relative to these components, light from the sample region reaching the receiver may be transmitted light, backscattered light, reflected light. Receiver 216 is operatively configured to sense multiple pre-determined sub-bands of the pre-selected absorption band(s) of interest, either simultaneously {or sequentially relative to each other}. It is noted that a sub-band may be a single frequency, but is more typically a range of frequencies. By sensing multiple sub-bands of the high-intensity absorption band(s) of interest, the resolution of the absorption characteristics of analyte(s) 204 of interest can be greatly improved over conventional detectors, such as the Nelson et al. scanning-type detector described above in the Background section.

In general, the present inventor has found that biological identification is best performed at frequencies from 400 (25 micron wavelength) to 4,000 wavenumbers (2.5 micron wavelength) at a spectral resolution of 4 wavenumbers. That is to say it is presently appears that sensor 200 should collect spectral information at approximately 900 wavelength bands in order to perform reliable biological agent identification. In addition, the spectral regions from 600 to 1,400 wavenumbers are particularly useful in identifying biological organisms. This region may be particularly useful because chemical compounds such as amides, polysaccharides, ribonucleic acid (RNA), deoxyribonucleic acid (DNA), useful for identifying organisms have spectral features in this region. Furthermore, the spectral region from 1,600 to 1,800 wavenumbers is also particularly useful in identifying biological organisms. This region may be particularly useful because chemicals such as amides, proteins, and fatty acids, useful for identifying organisms have spectral features in this region. Considerably less spectral information can be used to identify chemical agents, 10 to 20 wavelengths generally being sufficient.

In the case of explosive vapors, such as 2,4-dinitrotoluene (2,4-DNT), that have sharp and comparatively unique spectral absorption bands, two wavelengths are sufficient for detection and identification. DNT is the primary vapor given off by the ubiquitous explosive trinitrotoluene (TNT). The chemical, 2,4-DNT has a sharp absorption peak near 1348 wavenumbers. After searching 220,000 chemical spectra only 50 chemicals were found that had a peak near 1,348 wavenumbers and most of these chemicals turned out to be other isomers of DNT or explosives such as TNT or dinitrobenzene (DNB). Therefore, in the present invention explosives and their vapors may be detected by illuminating with light at a frequency of 1,348 wavenumbers that would be strongly absorbed by explosives or their vapors and with a second light beam near 1,348 wavenumbers, but off of the absorption peak. Detection may then be performed by comparing the received signal strength of the two beams. If no explosives or no explosive vapor is present, the normalized detected signal should be the same for the two beams. The normalization may take the form of comparing the returned pulse amplitude with the originally transmitted pulse amplitude. If explosives or explosive vapor is present, the beam at the wavelength of the absorption peak should be strongly attenuated. In fact, the amount of attenuation of the 1,348 wavenumber beam can be used to quantify the amount of explosive or explosive vapor encountered by the beam. Spectral resolution for reliable explosive detection generally requires a spectral resolution of 4 wavenumbers or better. The better the resolution, the more rejection of interferents, which leads to improved selectivity.

Figure 3A:
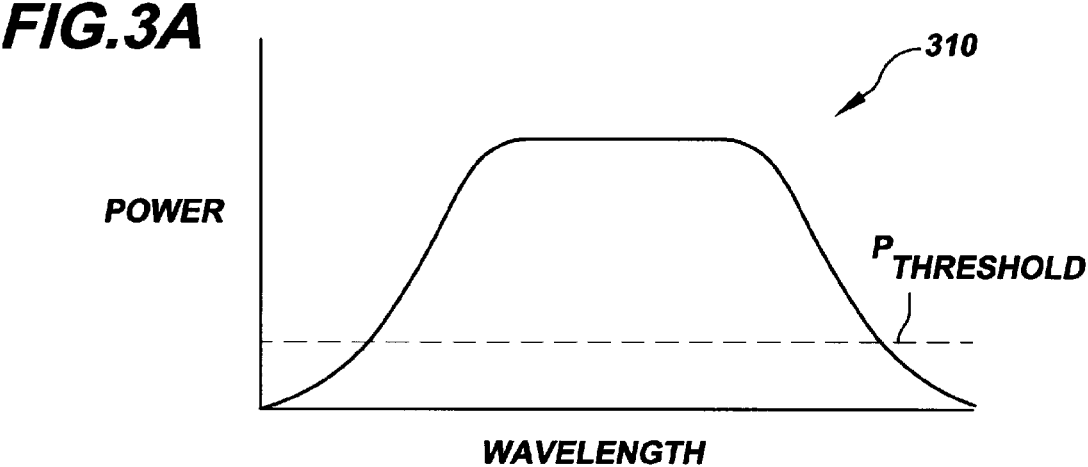
FIG. 3A is a plot of output power versus wavelength for a quantum cascade laser as used in an analyte sensor of the present invention.
Figure 3B:
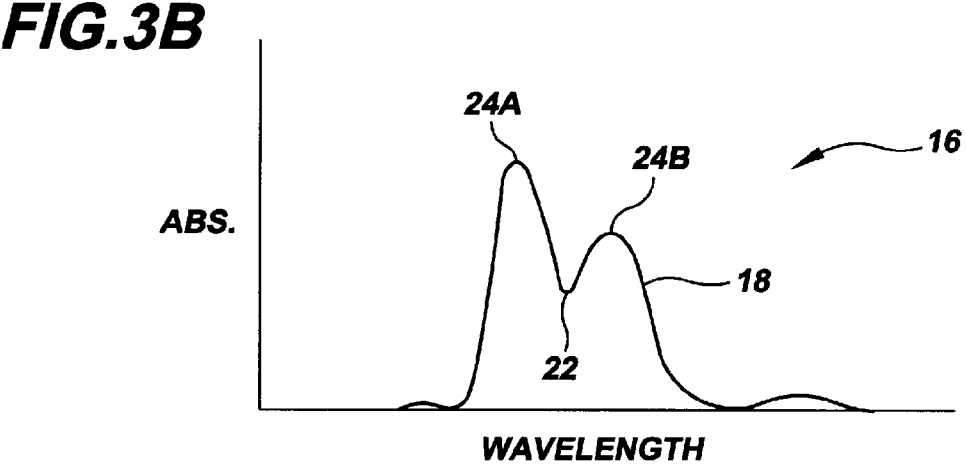
FIG. 3B, which is identical to FIG. 1B, is a plot of the spectral absorption characteristic of the exemplary compound of FIG. 1B.
Figure 3C:
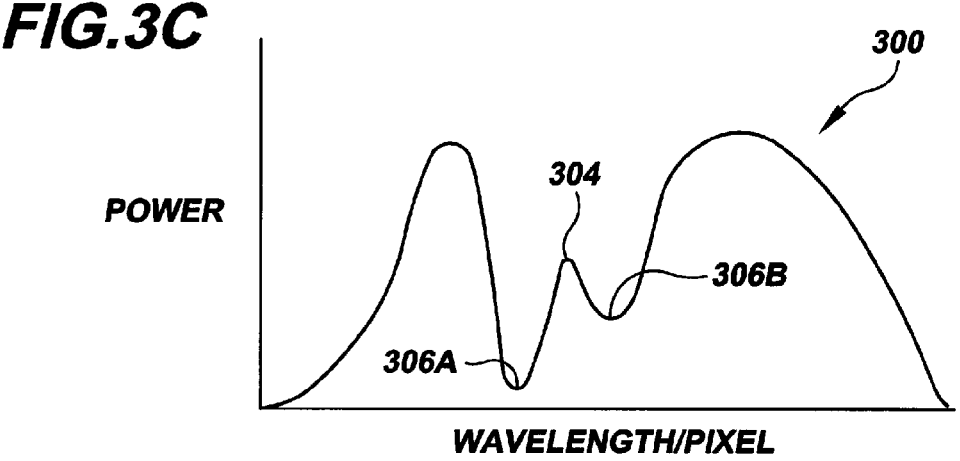
FIG. 3C is a plot of the detected spectral transmission of the light output from the quantum cascade laser of FIG. 3A as measured by a receiver of the present invention.

Referring to FIGS. 3A-3C, FIG. 3C illustrates advantages of using a sensor of the present invention, such as detector 200 of FIG. 2, as opposed to a prior art sensor, such as the Nelson et al. detector described above in the Background section. FIG. 3B is identical to FIG. 1C and shows a plot 16 of the absorption profile 18 of carbon dioxide over a range of wavelengths. Again, note the prominence of features, such as valley 22, peak 24A (which is at 2,360 wavenumbers/4.2373 microns), and peak 24B (which is at 2,340 wavenumbers/ 4.2375 microns). FIG. 3C is the counterpart of FIG. 1D and shows a plot 300 of the detected portion of the light after the light has interacted with the carbon dioxide analyte. Essentially, plot 300 is a plot of the light transmitted through the carbon dioxide over the spectral band at issue as measured by a sensor of the present invention, such as sensor 200. Note the strong correspondence of plot 300 to plot 16 (FIG. 3B) of the chemical absorption profile 18. It is particularly noted that features 304, 306A, 306B of plot in FIG. 3C are well-defined and virtually identical in form to the actual features 22, 24A, 24B of plot 16 in FIG. 1C.

Figure 1A:
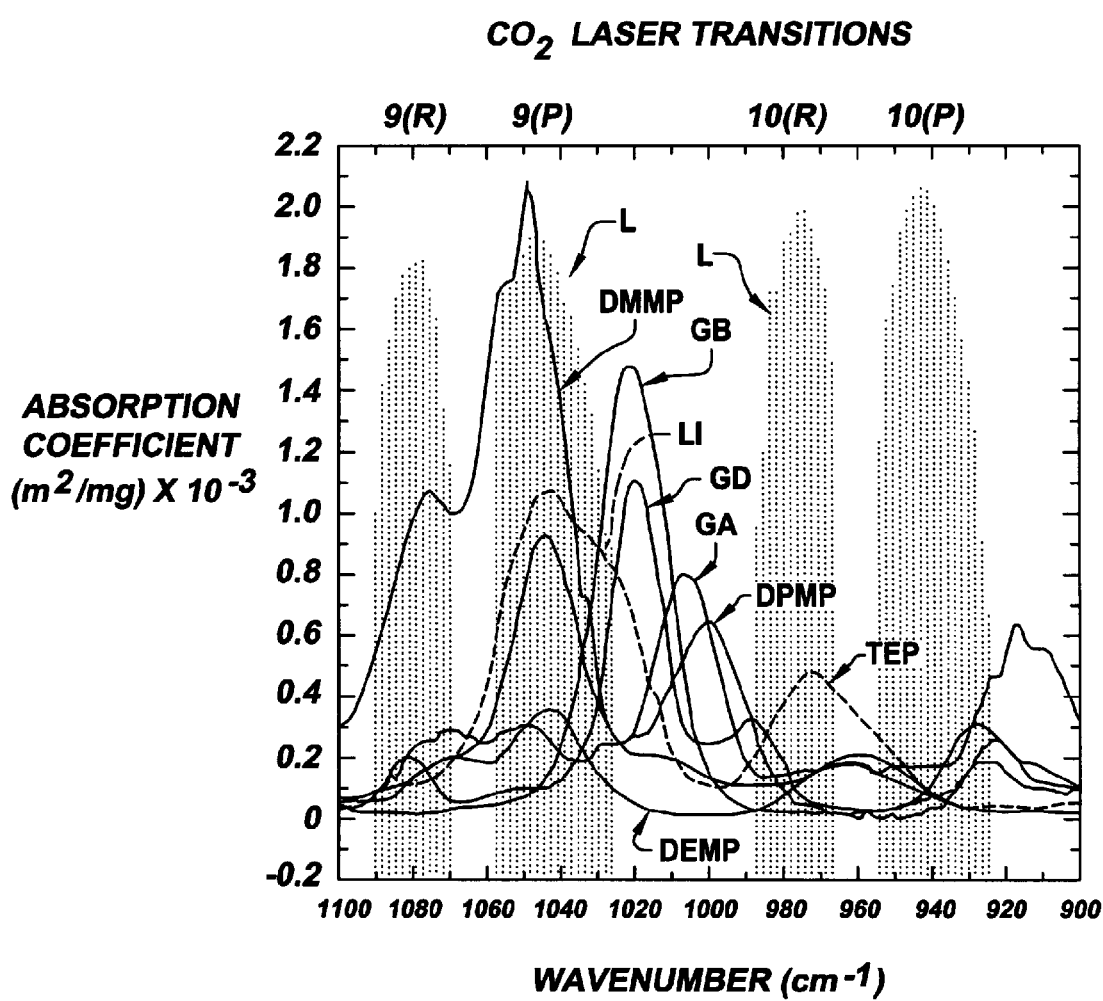
FIG. 1A is a plot of the spectral absorption of chemical warfare agents showing the wavelength of laser lines produced by a carbon dioxide laser.
Figure 1B:
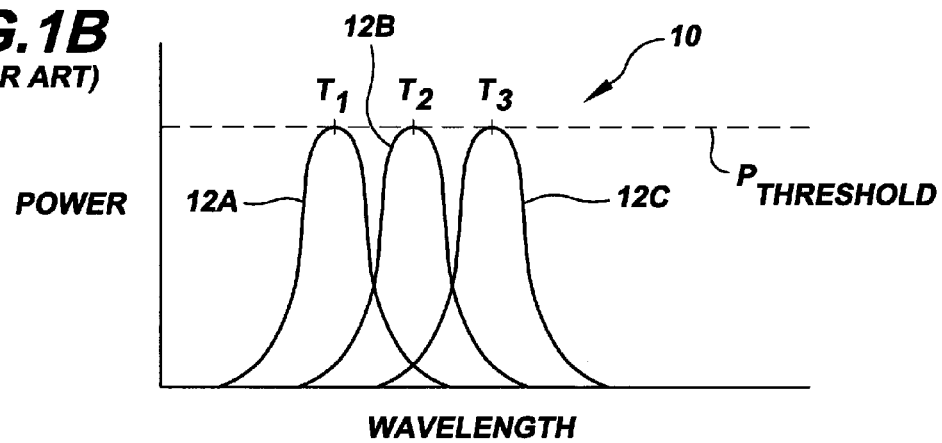
FIG. 1B is a plot of output power versus wavelength for a quantum cascade laser as used in a prior art detection system.
Figure 1C:
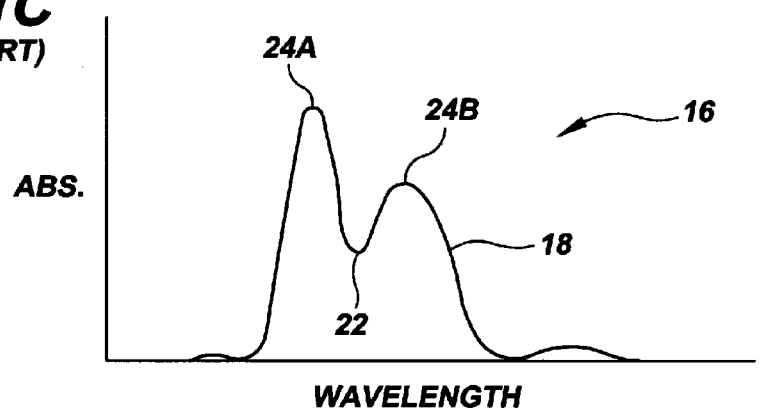
FIG. 1C is a plot of a spectral absorption characteristic of an exemplary compound to be detected by the conventional system of Nelson et al.
Figure 1D:
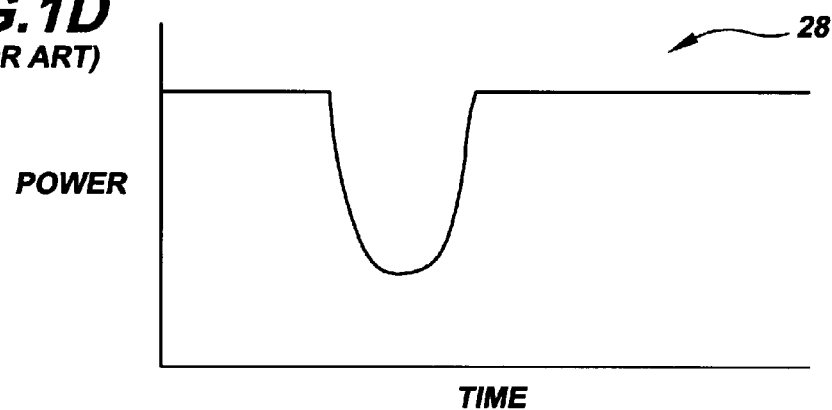
FIG. 1D is a plot of the detected spectral transmission of the light output from the quantum cascade laser pulses of FIG. 1B as measured by a conventional unfiltered broadband receiver over a period of time.

Importantly, contrast plot 300 of FIG. 3C obtained using a sensor of the present invention to plot 28 of FIG. 1D obtained using the state-of-the art Nelson detector. The vast superiority in the information obtained from plot 300 versus plot 28 as a representation of the actual absorption profile 18 (FIGS. 1C, and 3B) of carbon dioxide is readily apparent. Plot 300 of FIG. 3C virtually identically replicates features 22, 24A, 24B of FIG. 3B. Plot 28 of FIG. 1D, on the other hand, obscures features 22, 24A, 24B averaging them together. Since a sensor of the present invention can provide highly accurate and precise spectral absorption data, such a sensor can likewise provide very accurate and precise detection and identification capabilities that simply could not be achieved in the prior art due to feature blurring and other shortcomings. The present invention is not limited in resolution by the spectral linewidth of the illuminator, but rather by the spectra resolution of the detector filter.

Referring to FIG. 3A, an important feature of the present invention is the use of an illuminator, e.g., illuminator 212 of FIG. 2, that illuminates analyte(s) 204 of interest with high intensity light across at least the spectral band of interest, in this case about 4.2 microns to about 4.4 microns. The illuminator may be a Fabry-Perot quantum cascade laser. Referring to FIG. 1A, recall that to achieve good results using a broadband receiver, Nelson et al. needed to drive their QC laser so that the output power barely exceeded the threshold power $P_{THRESHOLD}$ of the laser. This is in contrast to the output power of the QC laser used in the present invention that is desired to be greater than the threshold power $P_{THRESHOLD}$ of the laser. In fact, in a sensor of the present invention it can be highly desirable to drive the QC laser so that the output power of the laser is relatively much higher than its threshold power. This is so because the higher the output power, and therefore intensity, the greater the levels of sensitivity, range and dynamic range can be achieved. In plot 310 of FIG. 3A it is seen that the QC laser is indeed driven to produce an output power about 4 times its threshold output power. In addition, because in the prior art approach the sensor resolution is limited by the laser spectral linewidth, a distributed feedback type quantum cascade laser had to be used. Distributed feedback lasers have a narrower spectral linewidth (18 wavenumbers) but produce approximately 4 times less power than Fabry-Perot type lasers, which have a linewidth of approximately 45 wavenumbers. Therefore, the present invention can use a light source with 16 times more intensity than the Nelson et. al. approach without sacrificing spectral resolution. It is noted that while the benefits of a detector of the present invention over a particular conventional sensor are described in the context of using a QC laser as the illumination source, it is noted that similar superior results can be achieved with other light sources as well. Some examples of alternative light sources are provided below.

In addition to illuminating the analyte in a manner much different than in the conventional detection systems, another important feature of the present invention lay in the receiver, such as receiver 216 of FIG. 2. As mentioned above, a receiver of the present invention is designed to sense multiple predetermined sub-bands of the absorption band(s) of interest, either simultaneously or sequentially with one another. In general, this approach avoids the detrimental effects, such as feature blurring, that conventional broadband receivers impose upon the detector. In the context of the Nelson et al. detector, their broadband receiver is a power integrator that, when scanning the laser pulses of FIG. 1A, causes spectral features to be blurred, as readily seen in FIG. 1C. Sensing sub-bands of relatively broadband spectral energy separately reduces such blurring. Various examples of receivers capable of sensing multiple sub-bands of the spectral band(s) of interest are described and listed below in connection with FIGS. 4A-4E.

Referring again to FIG. 2, illuminator 212 may comprise one or more illumination sources 220 and one or more drivers 224 operatively configured to drive the source(s) so that they emit the appropriate level of illumination across the desired spectral band(s). Driver(s) 224 is/are operatively configured to drive source(s) 220 so that all of the source(s) singly or together emit all of the wavelengths across each of the entire desired spectral bands (and likely some additional wavelengths either incidentally or by design) simultaneously with one another. Generally, for many analytes 204 of interest, it has been found that the spectral band containing the most useful spectral absorption information is the mid-infrared (mid-IR) band, which, for the present disclosure, extends from about 2.5 microns to about 25 microns.

Indeed, the present inventor has found that mid-IR light is particularly useful for remote sensing of aerosolized analytes or vapors. Mid-IR light is generally preferred for three reasons. First, chemical and biological matter generally have strong and unique mid-IR absorption characteristics, which allow a system of the present invention, such as system of FIG. 2, to detect and identify an analyte of interest with high selectivity by virtue of the improved spectral resolution of a sensor of the present invention. Second, these mid-IR absorption characteristics are typically three or more orders of magnitude stronger than the absorption characteristics in the near-IR band. This increased absorption strength translates into higher sensitivity. Third, the mid-IR band contains low-loss atmospheric transmission windows, generally at wavelengths between about 3 microns and about 5 microns and between about 8 microns and about 14 microns, resulting in improved sensitivity and detection range. Losses in these windows are so low that detection and identification of analytes on or near the Earth's surface may be accomplished from a satellite orbiting the Earth. That said, for some applications, light in other spectral bands may be preferred. For example, far-IR light is better than mid-IR light at penetrating solid materials, e.g., fabrics used to make clothing and luggage. Therefore, far-IR light may be preferred for applications such as passenger screening and baggage screening. Those skilled in the art will understand the relationship between the wavelengths of the light used to illuminate a region that may contain one or more analytes of interest and the particular analyte(s) of interest.

Consequently, illuminator 212 will vary depending on the demands of the particular application of sensor 200 that will typically include sensitivity, selectivity, response time, range, cost and operating environment, among others. For the purpose of illustration and not limitation, exemplary devices suitable for use as an illumination source 220 include, but are not limited to, mid-IR sources such as quantum cascade (QC) lasers, lead salt lasers, grating tuned carbon dioxide lasers, antimonide lasers, germanium lasers, glow bars, beryllium lasers, and optical parametric amplifiers, among others. Parametric amplifiers and lasers each have the advantage that they are wavelength tunable and have a relatively high spectral intensity. Glow bars are generally inexpensive and broadband, but lack spectral intensity. In the embodiments described herein, illumination source(s) 220 comprises one or more QC lasers, which are presently preferred because QC lasers are continuously tunable, have relatively high output power, are efficient and compact and operate in a comparatively high ambient temperature, thereby reducing cooling costs and power requirements. Based on the below description of the present invention in the context of QC lasers, those skilled in the art will understand the modifications necessary to implement any other suitable illumination devices as source(s) 220, including the devices listed above.

As mentioned several times above, receiver 216 of FIG. 2 is operatively configured to sense multiple sub-bands of the spectral energy emitted by illuminator 212. The sensing of multiple sub-bands may be accomplished using a detector 228 that may be any one of a variety of detectors. For example, referring to FIG. 4A, in one embodiment a receiver 400 suitable for use as receiver 216 may include a detector array 404 and a filter 408 located in the path of light exiting sample region 208 (FIG. 2) after interacting with the material within the region. In a preferred embodiment, filter 408 is fixedly attached to detector array 404 so as to provide a solid state receiver 400 that is robust and insensitive to external influences, such as vibration. That said, in alternative embodiments, filter 404 need not be applied directly to detector array 400. In the embodiment shown, detector array 404 may be, e.g., a pyroelectric array, a quantum well infrared photodetector (QWIP) array or a microbolometer array, photoconductor array, among others, and filter 408 may be a linear variable interference filter applied directly to the array. A linear variable interference filter acts as a band-pass filter for each pixel element 412 of detector array 404 such that each pixel element detects a different wavelength band, i.e., sub-band of the spectral energy emitted by illuminator 212 (FIG. 2).

Figure 4C:
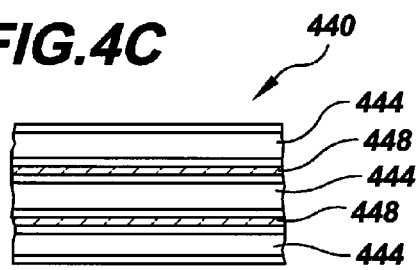
FIG. 4C is a cross-sectional view of a stacked tunable filter suitable for use with the sensor array of FIG. 4B.
Figure 4A:
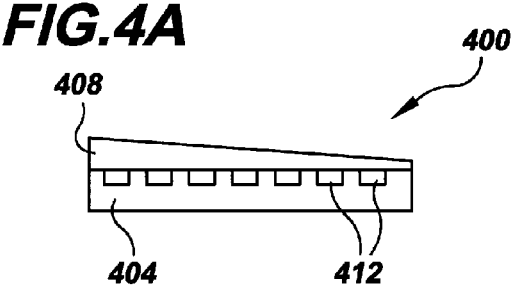
FIG. 4A is a cross-sectional view of a receiver suitable for use in the detector of FIG. 2 and including a linear variable filter.

In one embodiment, the output of each pixel element 412 of detector array 404 is digitized by a digital signal processor (DSP) 232 (FIG. 2) that generates a digitized spectral data vector 236 (FIG. 2) containing, e.g., spectral intensity data from all pixel elements 412 in detector array 404. This spectral data vector 236 may then be utilized by an analyzer 240 (FIG. 2) in detecting an identifying analyte(s) 204 of interest that may be present within sample region 208 (FIG. 2). Receiver 400 of FIG. 4A is an example of a receiver in which spectral information for all sub-bands at issue is captured by the receiver simultaneously. This characteristic of receiver 400 can result in savings in time needed to collect the spectral data needed for detection and identification resulting in improved detection time. An alternative to filter 408 being a linear variable interference filter is the filter being a diffraction grating (not shown) or tunable filter.

Figure 4D:
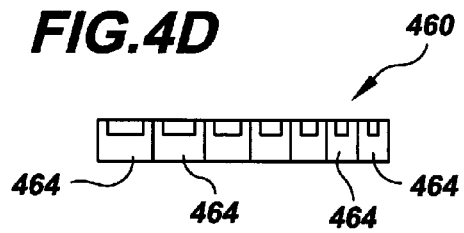
FIG. 4D is a cross-sectional view of another receiver suitable for use in the detector of FIG. 2 and including individually tuned pixel detectors.
Figure 4B:
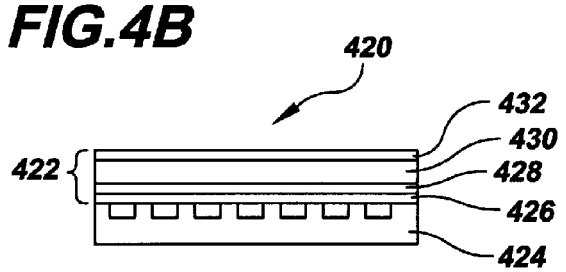
FIG. 4B is a cross-sectional view of an alternative receiver suitable for use in the detector of FIG. 2 and including a tunable filter.

Referring to FIG. 4B, in an alternative solid state receiver 420 suitable for use as receiver 216 of FIG. 2, a filter 422 may be applied directly to sensor array 424. However, instead of filter 422 being a linear variable interference filter, it may be a tunable filter comprising a dielectric layer 426, a first conducting layer 428, an electro-optic layer 430 and a second conducting layer 432. Dielectric layer 426 provides electrical insulation between first conducting layer 428 and sensor array 424. The choice of material for dielectric layer 426 will generally depend upon the wavelengths required for a particular application. Dielectric layer 426 will typically be transparent to the wavelengths of energy to be sensed. Examples of materials that can be used for dielectric layer 426 include diamond, zinc selenide, germanium, AMTIR, KRS-5, Cadmium telluride, silver chloride, zinc sulfide, calcium flouride, lithium flouride, strontium flouride, barium flouride, cesium bromide, potassium chloride, potassium bromide, cesium iodide, magnesium oxide, sodium chloride, gallium arsenide, silicon, polyethylene, magnesium fluoride, spin-on glass and polyimide, among others. First conducting layer 428, like dielectric layer 426, will typically be transparent to the wavelengths to be detected and should be a good conductor. By way of illustration, and not limitation, first conducting layer 428 may be indium tin oxide or a thin layer of gold.

Like dielectric layer 426, the material for electro-optic layer 430 will generally be chosen based on its transparency to the wavelengths to be sensed by sensor array 424. Examples of electro-optic materials that may be used include, but are not limited to, Selenium, CdTe, GaAs, GaP, ZnS, ZnSe, ZnTe, $Bi_{12}SiO_{20}$, PLZT, $LiO_3$, $AG_3AsS_3$, $LiNbO_3$, $LiTaO_3$, $AgGaS_2$, $CsH_2AsO_4$ (CDA), KDP, KTP, ADP, $BaTiO_3$, KTN, $HIO_3$, $KNbO_3$ and $KIO_3$. The material for second conducting layer 432 may be selected in the same manner as first conducting layer 428 described above. Referring to FIG. 4C, it is noted that additional similar layers can be provided to create a multi-layer stacked filter 440, or mirror having multiple electro-optic layers 444 electrically isolated from one another by respective dielectric layers 448. Such a stacked filter/mirror 440 can have improved characteristics such as a narrower full width half max, a broader full width half max, or the ability to filter the same wavelength at multiple angles of incidence.

Referring again to FIG. 4B, filter 420 is tunable by virtue of the electro-optic layer 430. Electro-optic materials change their refractive index, n, depending upon the voltage applied across first and second conducting layers 428, 432. This change is governed by the formula:

$$\Delta n = \frac{rEn^3}{2} \quad (1)$$

wherein $\Delta n$ is the change in index of refraction, r is the electro-optic constant, which is a property of the material, and a function of wavelength and E is the applied electric field.

For example, for a single electro-optic layer 430 as shown in FIG. 4B, if the layer is made of KTN (n=2.318, r=8e-9 m/V) that is 68.27 nm thick, the layer will act like an anti-reflection layer for normal incident light with a wavelength of 0.633 microns (0.633/4=0.06827×2.318). However, by applying a voltage of 0.1 V across electro-optic KTN layer 430, its refractive index is shifted by 0.5×8e-9(0.1/68.27e-9)(2.318)³=0.07297. This results in electro-optic layer 430 acting like an anti-reflection layer for light at normal incidence shifted by about 20 nm. Larger shifts can be achieved by applying larger voltages. This example should make clear that tunable electro-optic filter 422 may be applied to detector array 424 to give the array the ability to gather spectral information. By stepping in time the voltage applied across the one or more electro-optic layers 430, detector array 424 can sweep through sensing different wavelengths. Furthermore the electrodes may be patterned so that the filters in the array are individually addressable.

Receiver 420 is an example of a receiver that collects spectral information serially, rather than simultaneously as is done in receiver 400 of FIG. 4A. The serial nature of receiver 420 may have a slight impact on performance of a detector of the present invention that utilizes such a receiver. However, in the case where tunable filter 422 is tunable for detecting a variety of analytes across a variety of spectral sub-bands, any decrease in performance will generally be outweighed by the sheer versatility and robustness of receiver 420.

It is noted that tunable filters of the present invention, such as tunable filters 422, 440 of FIGS. 4B and 4C, respectively, may have many uses outside of a sensor of the present invention, such as sensor 200 of FIG. 2. For example, a tunable filter of the present invention may be used as a tunable dielectric mirror for tuning the wavelength of laser output. It could also be used as a means for Q-switching or cavity dumping. In addition, a tunable filter of the present invention has uses in hyperspectral imaging, non-destructive testing, target discrimination, etc. For example, a tunable filter of the present invention could be used to decrease clutter and better identify and track targets in high-clutter environments. The tunable filter can be used to enable a single FLIR array to capture spectral information.

In alternative embodiments, receiver 216 may not utilize a filter. For example, FIG. 4D shows a receiver 460 suitable for use with detector 200 of FIG. 2. In this embodiment, receiver 460 includes an array of sensors, e.g., pixel detectors 464, in which the detectors are manufactured, or tuned, to sense corresponding sub-bands of the spectral energy emitted by illuminator 212 (FIG. 2). Such differences in the spectral response of receiver 460 may be implemented by doping the pixel detectors 464 differently or by using a diffraction grating (not shown) to spatially separate spectral bands on the pixel array. This is in contrast to detector arrays 404, 424 of FIGS. 4A and 4B in which all pixel elements 412 (FIG. 4A) of the arrays are broadband sensors, which are subsequently narrowed by an external filter arrangement. In the case, receiver 460 will behave like receiver 400 of FIG. 4A in that the spectral information across all sub-bands at issue will be sensed simultaneously with one another.

Figure 4E:
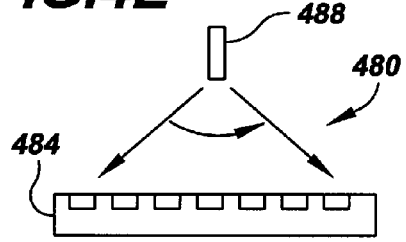
FIG. 4E is a cross-sectional view of yet another receiver suitable for use in the detector of FIG. 2 and including a scanning device.

Referring to FIG. 4E, in another example of a receiver 480 suitable for use as receiver 216 of FIG. 2 but not using a filter, sensor array 484 may be a broadband array, which may be used to serially sense different wavelength energy as a scanning device 488, e.g., a Michelson interferometer, acousto-optic filter, SAW filter, or Fabry-Perot cavity, among others, scans through the spectral range at issue and focuses the scanned energy onto the sensor array. In this manner spectral information across the sub-bands at issue is sensed serially in a manner generally similar to receiver 420 of FIG. 4B in the case where the tunable filter is not individually addressable. Again, serial sensing can result in slight decrease in performance. In addition, it is noted that a receiver that includes a scanning device, such as scanning device 488, will typically be more susceptible to movement, such as vibration and jarring. These factors should be taken into consideration when designing a detector of the present invention.

Referring again to FIG. 2, as mentioned above receiver 216 may include DSP 232 that outputs to analyzer 240 a digitized spectral data vector 236 corresponding to the sampled matter present in sample region 208. Analyzer 240 may be configured (i.e., hardwired and/or programmed) to process spectral data vector 236 in any of a number of manners that allows it to determine the presence of the analyte(s) 204 of interest in the sampled matter and, optionally, to identify the one or more analytes. For example, analyzer 240 may include software 244 that performs a method of the present invention, such as a method of detecting and identifying the analyte(s) 204 of interest, e.g., by partial least squares matching or alternatively by discriminant analysis. Other analyses that analyzer 240 may perform, particularly in the context of aerosolized particles, are particle sizing and particle mapping. Both of these methods are described below.

A method of detecting and identifying an analyte may generally include taking the derivative of spectral data vector 236 of the sample to obtain a derivative vector. Initially, the first derivative of the data in spectral data vector 236 can be produced by computing the slope between each adjacent pair of received spectral sub-band intensities contained in the data vector. For example, let n be the number of pixels in sensor array 228, let $P_i$ be the power received by the ith pixel in the array and let $\lambda_i$ be the wavelength (alternatively, frequency may be used) of the ith pixel, then the slope $M_i$ is given by:

$$M_i = \frac{P_i - P_{i+1}}{\lambda_i - \lambda_{i+1}} \quad \{2\}$$

The slope M is essentially the differential received power, which is related to the differential absorption spectra of the sample. Taking the first derivative simplifies identification of the analyte 204 of interest by eliminating intensity shifts that can be caused by differences in concentration of the sample, aging of the light source, etc. The second derivative can be computed in a similar manner by computing the slope of the slope M. The present inventor has found, however, that the first derivative of the data in spectral data vector 236 is usually sufficient for reliable analysis for many applications.

After computing the derivative of the sample spectra data in spectral data vector 236, the resulting sample slope vector, i.e., $[M_1, M_2, M_3, \ldots M_{n-1}]$, may be multiplied by a number of canonical variate vectors. (The method of generating canonical variate vectors is described in detail below.) This multiplication transforms the sample derivative vector into a reduced dimension vector, which can be thought of as a point in canonical variate space. Next, the Mahalanobis distances are computed between the resulting data point of the sample and the like data points of known groups. The unknown sample is preliminarily assigned to the known group having the smallest Mahalanobis distance from the data point of the sample. Next, if the Mahalanobis distance is less than or equal to the greatest within-group Mahalanobis distance of the preliminarily assigned group, then the sample is identified as belonging to that group. If, on the other hand, the Mahalanobis distance is greater than the within-group distance, then the sample is identified as belonging to an unknown group. However, the Mahalanobis distance of the unknown to each respective group may be reported. The canonical variate vectors may be produced by multivariate discriminate analysis of the spectral slope vectors of known groups.

For example, if it is desired that a detector of the present invention identify anthrax, tularemia and plague, then a large number of samples for each organism should be prepared and spectral data for each sample should be collected in a corresponding digitized spectral data vector. A slope vector is then computed for each spectral data vector as described above. Next, multivariate discriminate analysis is applied to these known slope vectors. As a result of the analysis, each known sample can be plotted in canonical variate space as described above and each group centroid can be plotted as a point in this space. These same canonical vectors are used to transform a future sample to be identified into a point in the canonical variate space, wherefrom the Mahalanobis distance of the sample point and the known species centroid points can be computed. It is noted that once the derivative of spectral data vector has been obtained, the canonical variate vector analysis described above can be performed using well know techniques. In fact, this analysis can be performed using conventional statistical analysis software, such as the JMP® statistical software package available from SAS Institute Inc., Cary, N.C.

In a particular example, the present inventor implemented the foregoing method for automating the identification of closely related bacterial species based on their infrared (IR) transmission spectra. This example involved the analysis of IR transmission spectra of 108 bacterial samples from seven *Bacillus* species (*B. cereus, B. sphaericus, B. subtilis, B. licheniformis, B. laterosporus, B. amyloliquefaciens*, and *B. megaterium*). The spectra of each sample was taken from four thousand wavenumbers to four hundred seventy six wavenumbers at a spectral resolution of four wavenumber, resulting in eight hundred eighty two data points in each spectral data vector 236 for each sample. The first derivative of each spectral data vector 236 was then computed in the manner discussed above. A multivariate analysis was then used to convert the 108×882 data matrix into seven sets mapped into six dimensions corresponding to the maximal discrimination between species groups. Generally, the multivariate analysis will map the points into a dimensional space having a dimension one less than the number of species groups.

In the multivariate analysis, the between-group sum of squares and products matrix was computed, and the within-group sum of squares and product matrix was computed. These matrices were then used to derive expressions for the mean square ratio. Next, the first derivative of this expression was taken and set to zero. The resulting expressions were then solved, producing coefficients for each wavelength. The resulting coefficients vectors are multiplied with the derivative vectors producing a linear combination of the original wavelength data called the canonical variates. This vector multiplication of the derivative vectors and coefficients transforms the data into the canonical variate space. The transformed derivative IR spectra was then plotted in this new canonical variate space and distances between bacterial samples and species groups were then computed using the Mahalanobis distance to get a better understanding of the true discriminant differences between data points. Unknown bacteria were identified by converting their IR spectra into the canonical variate space (using the same wavelength coefficients) and preliminarily assigning them to the closest species group based on the computed Mahalanobis distance. The Mahalanobis distance of the unknown sample is then compared to the within species variance in the Mahalanobis distance. If the distance was within-species variance, the sample preliminary assignment was confirmed. If not, the sample was classified as not from a known group.

Figure 11:
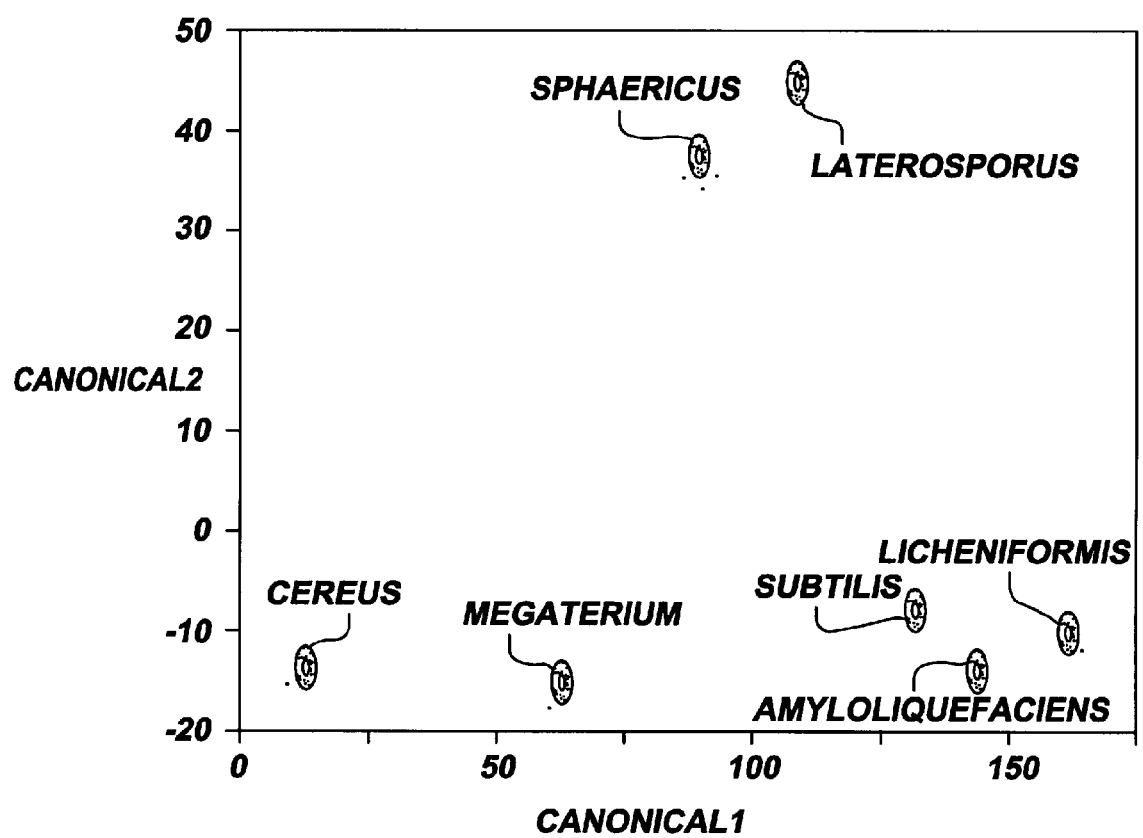
FIG. 11 is a plot of one hundred eight bacterial samples from seven species versus two canonical variates.

FIG. 11 is a plot of the 108 bacterial samples against just two canonical variates using only wavelengths emitted from commercially available QC lasers. From FIG. 11 it can be readily seen that the first canonical variate provides excellent separation among the seven species of bacteria, but by using additional variates additional discrimination can be provided. In the course of the present implementation, the present inventor observed that the ability to discriminate among bacteria species appears to be dependent upon the number of wavelength data points used. The more wavelengths used, the better the discrimination. Generally, this provides evidence that a broad-spectrum approach is desirable to successfully identify bacteria.

Figure 12:
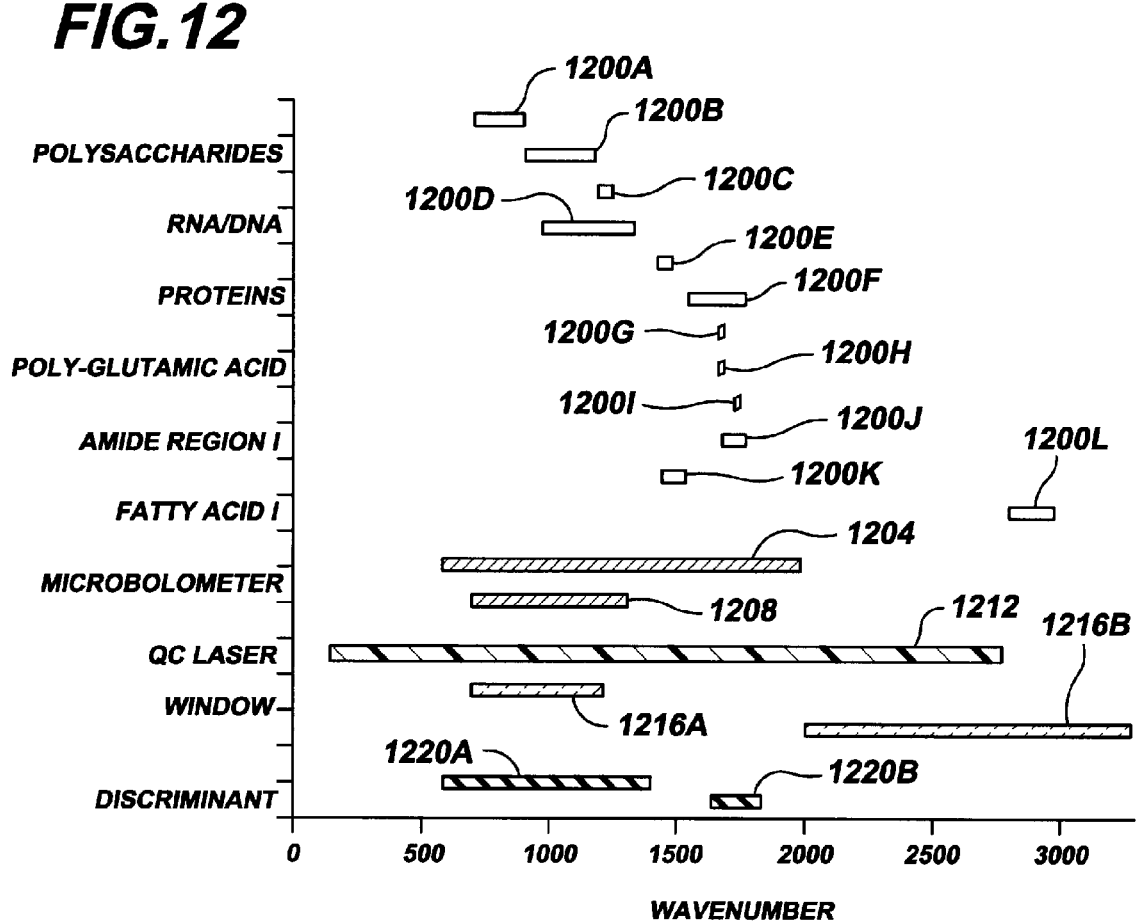
FIG. 12 is a graph showing the relationships among spectral bands of: chemical absorption for various analytes; operation of conventional cooled and un-cooled microbolometers; operation of presently available QC lasers; low-loss atmospheric transmission windows; and frequencies found useful for bacteria discrimination.

FIG. 12 is a graph showing the relationships among spectral bands of: chemical absorption for various analytes (1200A-L); operation of conventional cooled (1204) and un-cooled (1208) microbolometers; operation of presently available Fabry-Perot QC lasers (1212); atmospheric windows (1216A-B); and the frequencies most useful for bacteria discrimination (1220A-B). As can be seen from FIG. 12, there is considerable overlap between wavelengths: that can be produced by a Fabry-Perot quantum cascade laser (1212), that can be detected by un-cooled microbolometers (1208), that are useful for bacterial species discrimination (1220A-B), and have low loss atmospheric transmission (1216A-B). The wavelengths most useful for discrimination may be attributable to the vibrational absorption of unique chemicals present in each species. These vibrational absorption regions include DNA/RNA sugar backbone vibrations, amides, polysaccharides, proteins, and fatty acids. For example, poly-glutamic acid is of particular interest because it has been shown to be essential to virulence in anthrax. It is noted that when the illuminator of a sensor of the present invention, e.g., illuminator 212 of sensor 200 shown in FIG. 2, is relatively powerful, a system of the present invention can detect analytes, including bacteria, from a large range of distances, from immediately adjacent a sample region to tens, hundreds, or thousands of meters or more. This fact is particularly impressive in the case of bacteria identification, since, to the best of the present inventor's knowledge, the maximum range of bacteria identification using conventional sensors is no more than about one meter. Moreover, as mentioned above, a sensor of the present invention can be made into a handheld unit that is substantially insensitive to vibrations that would typically be experienced by sensors deployed in the field.

It is often desirable to perform the discriminate analysis on sample spectra having as wide a signature variability as possible in order to ensure a robust algorithm. This is particularly the case when an analyte of interest involves bacteria. It is known that growth conditions of bacteria, including growth media, can create signature variability in bacteria. Using the foregoing analysis and the portion of the spectral absorption signature having the widest variability can lead to perfect species characterization.

In addition, it can be useful to collect and analyze common interferents for the analyte(s) of interest in order to reduce the rate of false positive identification. For example, *Bacillus subtilis* is a common (and benign) interferent for detecting *Bacillus anthracis* (anthrax). Consequently, when developing canonical variate vectors for detecting anthrax, it is desirable to collect spectral data for *Bacillus subtilis* to maximize the ability of analyzer to distinguish between the analyte (anthrax) and its interferent (*Bacillus subtilis*). Collecting and considering interferents when analyzing spectral data from a sample is also useful in detecting and identifying various chemical compounds.

For example, detector 200 may be used for the roadside detection of the presence of bombs aboard vehicles passing a checkpoint. In this case, detector 200 may be configured to detect the presence of one or more materials, i.e., analyte(s) 204, that would indicate the presence of a bomb, such as TNT, its more volatile degradation product dinitrotoluene (DNT) and/or its even more volatile commercial tagant mononitrotoluene (MNT). However, common chemicals present in vehicle exhaust, such as toluene, benzene and xylene, among others, have spectral signatures that include some spectral features that are common to, and some spectral features that are distinct from, the analyte(s) of interest, e.g., TNT, DNT and MNT, and are, therefore, characterized as interferents for these analytes. Consequently, false positive identifications can be reduced by avoiding reliance on spectral features common to interferents likely to be present at the checkpoint during sampling. As yet another example, organo-phosphate insecticides such as malathion and parathion may act as interferents in the detection of nerve agents such as Sarin, Tabun and Soman, among others.

Referring still to FIG. 2, detector 200 may further include a system controller 248 for coordinating and controlling the operations of illuminator 212, receiver 216 and analyzer 240. In general, the operational configuration and/or programming of system controller 248 will vary as a function of the type of illuminator 212 and receiver 216 utilized, the analysis that analyzer 240 performs, the additional features/components that sensor 200 may include, e.g. one or more displays, communications systems, data ports, operating controls, support systems, such as a cooler if illuminator utilizes a laser or other source requiring cooling, etc. Those having ordinary skill in the art will readily understand the functions that system controller 248 will need to perform for a particular sensor 200, depending upon the hardware and/or software utilized, such that an exhaustive description of the system controller is not necessary for such skilled artisan to make and use the present invention to its fullest scope. That said, a general example of basic functionality that system controller 248 may provide is coordination of the timing of the operation of analyzer 240 relative to receiver 216 and the timing of the operation of the receiver relative to the activation of illuminator 212 so that spectral data is acquired and analyzed in an effective and efficient manner. In addition, system controller 248 may be used to control tunable filter 422, 440 (FIGS. 4B and 4C) or scanning device 488 (FIG. 4E) when either of these components is present. Alternatively, the corresponding receiver 400, 420, 460, 480 may include a local controller (not shown) that locally controls tunable filter 422, 440 or scanning device 488 but is responsive to global control signals from system controller 248. System controller 248 may be implemented in a suitable processor, such as a general purpose microprocessor, application specific integrated circuit (ASIC) or system on chip (SOC), field programmable gate array (FPGA), among others.

In addition to analyzer 240 of FIG. 2 being operatively configured to detect and identify one or more analytes 204 of interest, it may additionally or alternatively be configured to determine the sizes of particles, e.g., when the analyte comprises aerosolized particles, within region 208. For many applications it is desirable to measure the size distribution of particles. For example, in anthrax detection, smaller particles represent a greater hazard as they are inhaled more deeply into the lung. Measuring the particle size distribution can provide quick characterization of the degree to which an anthrax sample is weaponized and the hazard it poses.

In the case in which the particles of interest are molecules, the particles will obey Rayleigh scattering. For example, Rayleigh scattering would occur for the detection of molecular vapors given off by explosives such as ethylene glycol dinitrate (EGDN). EGDN is a common byproduct found in nitroglycerine based explosives (dynamite) and is used as a tagant in other commercial explosives. For wavelengths far from strong absorptive bands, the scattering cross section, $C_{scatter}$, of a particle that is small compared to the wavelength is proportional to:

$$C_{scatter} \sim v^2/\lambda^4 \qquad \{3\}$$

where v is the volume per particle and λ is the wavelength of light. In order to ensure the particle size is probed by wavelengths far from the absorption bands, it is desirable to first identify the particle. After identifying the particle with the methods described previously, wavelengths that are not absorbed by the identified material may be used to determine the particle size as will be described further below.

For wavelengths far from a strong absorptive band, the amount of scattered light is given by:

$$P_s = P_o * (1 - e^{-NLC_{scatter}}) \qquad \{4\}$$

where $P_o$ is the initial illumination power, $P_s$ is the scattered power, N is the particle concentration (particles per unit volume) and L is the path length through the particles. Thus, from Equations 3 and 4 it can be seen that the received light for a given size particle will have a strong dependence on the wavelength. Furthermore, it can be seen that particle scattering is greatly reduced when the ratio of particle size to wavelength is small. Therefore by measuring the scattered light intensity at different wavelengths it is possible to ascertain the size distribution of particles.

For example, let us suppose that multiple co-propagating beams of different wavelengths pass through a cloud of particles composed of like matter. It is assumed that the particles are distributed into two different sizes: 2 microns in diameter and 3 microns in diameter. Then, using Equation 2 the relative scatter cross sections can be computed for the different particle sizes and wavelengths as shown in the following table.

Proportional Scatter Cross Section as a Function of Particle Size and Wavelength

| Wavelength (μm) | Proportional scatter cross section @ 2 μm particle size (arbitrary units) | Proportional scatter cross section @ 3 μm particle size (arbitrary units) |
|---|---|---|
| 1 | C(2, 1) = 64 | C(3, 1) = 729 |
| 2 | C(2, 2) = 4 | C(3, 2) = 45.6 |
| 3 | C(2, 3) = .790 | C(3, 3) = 9 |
| 4 | C(2, 4) = .250 | C(3, 4) = 2.85 |
| 5 | C(2, 5) = .102 | C(3, 5) = 1.17 |
| 6 | C(2, 6) = .049 | C(3, 6) = .563 |

-continued

Proportional Scatter Cross Section as a Function of Particle Size and Wavelength

| Wavelength (μm) | Proportional scatter cross section @ 2 μm particle size (arbitrary units) | Proportional scatter cross section @ 3 μm particle size (arbitrary units) |
|---|---|---|
| 7 | C(2, 7) = .027 | C(3, 7) = .303 |
| 8 | C(2, 8) = .016 | C(3, 8) = .177 |
| 9 | C(2, 9) = .010 | C(3, 9) = .111 |
| 10 | C(2, 10) = .006 | C(3, 10) = .0729 |

The scattered light received at each wavelength can be computed by adapting Equation 4. For example, $P_s$ (at 1 micron wavelength)=$P_s$ (by 2 micron particles, at 1 micron wavelength)+$P_s$ (by 3 micron particles, at 1 micron wavelength)

$P_s$ (at 1 micron wavelength)=$P_o\,(1-e^{-N(2)LC(2,1)_{scatter}}-e^{-N(3)LC(3,1)_{scatter}})$=$P_s$ (at 1 micron wavelength)=$P_o\,(1-e^{-N(2)LC(2,1)_{scatter}}-e^{-N(3)LC(3,1)_{scatter}})$ $P_s$ (at 2 micron wavelength)=$P_s$ (by 2 micron particles, at 2 micron wavelength)+$P_s$ (by 3 micron particles, at 2 micron wavelength)

$P_s$ (at 2 micron wavelength)=$P_o\,(1-e^{-N(2)LC(2,2)_{scatter}}-e^{-N(3)LC(3,2)_{scatter}})$ $P_s$ (at 3 micron wavelength)=$P_o\,(1-e^{-N(2)LC(2,3)_{scatter}}-e^{-N(3)LC(3,3)_{scatter}})$ $P_s$ (at 4 micron wavelength)=$P_o\,(1-e^{-N(2)LC(2,4)_{scatter}}-e^{-N(3)LC(3,4)_{scatter}})$ $P_s$ (at 5 micron wavelength)=$P_o\,(1-e^{-N(2)LC(2,5)_{scatter}}-e^{-N(3)LC(3,5)_{scatter}})$ $P_s$ (at 6 micron wavelength)=$P_o\,(1-e^{-N(2)LC(2,6)_{scatter}}-e^{-N(3)LC(3,6)_{scatter}})$ $P_s$ (at 7 micron wavelength)=$P_o\,(1-e^{-N(2)LC(2,7)_{scatter}}-e^{-N(3)LC(3,7)_{scatter}})$ $P_s$ (at 7 micron wavelength)=$P_o\,(1-e^{-N(2)LC(2,8)_{scatter}}-e^{-N(3)LC(3,8)_{scatter}})$ $P_s$ (at 9 micron wavelength)=$P_o\,(1-e^{-N(2)LC(2,9)_{scatter}}-e^{-N(3)LC(3,8)_{scatter}})$ $P_s$ (at 10 micron wavelength)=$P_o\,(1-e^{-N(2)LC(2,10)_{scatter}}-e^{-N(3)LC(3,10)_{scatter}})$, etc., where N(2) is the particle concentration of 2 micron particles, N(3) is the concentration of 3 micron particles, $C(2,1)_{scatter}$ is the scatter cross section for 2 micron particle size at a wavelength of 1 micron, $C(3,1)_{scatter}$ is the scatter cross section for 3 micron size particles at a wavelength of 1 micron, etc. Given that the beams are co-propagating they all travel through the same path length L.

The path length L can be taken as the distance light travels through the sample medium during the detector integration time. For air samples this can be taken as $3\times10^8$ meters times the sample integration time of the detector in seconds. Therefore, L is known. The scattered power received at each wavelength is measured and therefore known. The initial power is also measured and therefore known. FIG. 5, discussed below in detail, illustrates the use of a monitoring detector (572) to measure initial power. Alternatively, initial power can be measured, e.g., by placing a beam splitter (not shown) in the optical path of beam 520 and measuring the deflected power split off from beam 520. In one embodiment, the beam splitter only deflects the relatively small amount power necessary to perform monitoring, thereby leaving a majority of beam 520 un-deflected. The particle concentrations at each wavelength are the unknowns for which it is desired to solve. Consequently, there is one unknown for every particle size desired to be sorted through; in this example there are two unknowns, N(2) and N(3). The relationship between all the scattering cross sections are known from Equation 3. Therefore all the scattering cross sections can be broken up into a single unknown constant and a computable proportionality constant, where the proportionality constant is computed from Equation 3 using the wavelength and the particle size. The foregoing table contains examples of computed cross section proportionality constants for particle sizes of 2 microns and 3 microns and wavelengths from 1 micron to 10 microns. Therefore, there is one unknown concentration for each particle size and one unknown for the scattering cross section constant. In addition, there is one equation for each wavelength measurement. Therefore, the particle concentration for each particle size (let X be the number of particle sizes) and the scattering cross section constant can be solved for by measuring the scattered power for at least X+1 wavelengths. Therefore the particle size resolution is limited to one less than the number of wavelengths measured by sensor 228.

The largest particle size that can be identified will be limited to the shortest wavelength measured. For particles larger than the shortest wavelength begin exhibiting Mie scattering behavior rather than Rayleigh scattering behavior. The smallest particle size that can be identified will be limited by the shortest wavelength measured, the power of illuminating source(s) 220, the particle size concentration, and the noise equivalent power of detector 200.

Figure 5:
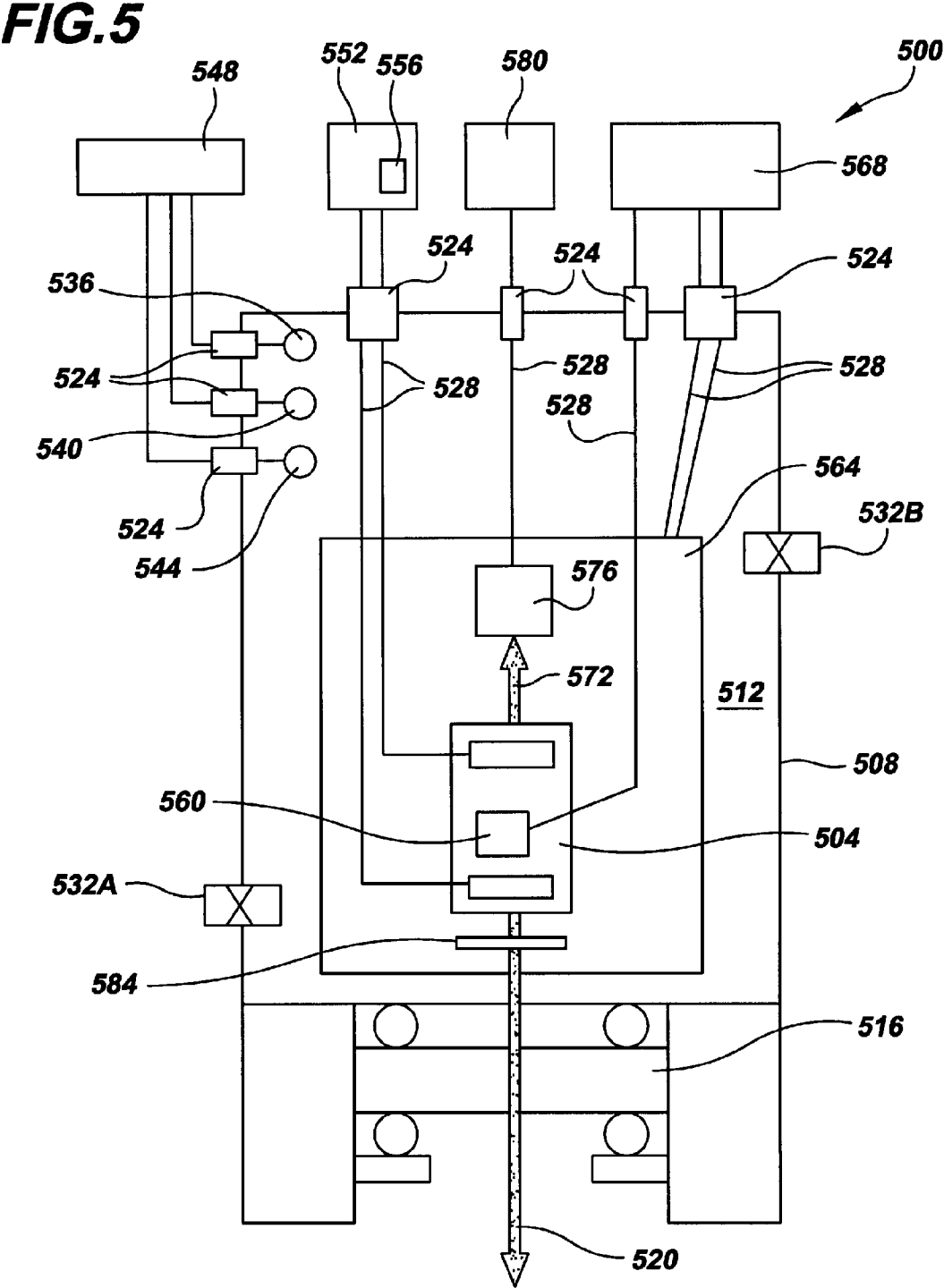
FIG. 5 is a schematic diagram of a particular illuminator of the present invention.

FIG. 5 illustrates a particular embodiment of an illuminator 500 that may be used in connection with a detector of the present invention, such as detector 200 of FIG. 2. Illuminator 500 has a number of features, e.g., robustness and relatively low power consumption, among others, that make it particularly desirable for use as a portable illuminator. However, it can also be used with fixed detecting and identifying systems, as well. Illuminator 500 generally comprises a QC laser diode 504 mounted inside a enclosure 508, which may be, e.g., an explosion-hardened enclosure. Enclosure 508 forms a vacuum-tight chamber 512 and includes a window 516 that allows passage of an output beam 520 of QC laser diode 504 out of the enclosure and further includes a plurality of vacuum-tight electrical feedthroughs 524 for various electrical conductors 528 to extend outside the enclosure. Since it is typically desirable to minimize the transfer of heat external to enclosure 508 into chamber 512, it may be desirable to make the electrical connections between internal and external electronics using a low thermally conductive connector, such as phosphor bronze wire. Window 516 may be made of any suitable material transparent to output beam 520. For purposes of illustration and not limitation, suitable materials for window 516 may include anti-reflection coated germanium with a diamond like coating overcoat, zinc selenide, germanium, diamond, thallium bromoiodide (KRS-5), polyethylene, and any of the materials listed above as dielectrics among others. When illuminator 500 needs to withstand rigorous use, diamond is a good choice for window 516 due to its high transparency over a broad spectral range, hardness and high damage threshold. If cost is an issue, a good alternative to diamond is anti-reflection coated germanium with a diamond like coating. This provides abrasion resistance at a lower cost than diamond.

Enclosure 508 may also include first and second valves 532A, 532B for purging the atmosphere inside the enclosure. For example, first valve 532A may be used to introduce dry nitrogen into chamber 512, and second valve 532B may be used to allow air and moisture to exit the chamber. When this is done, second valve 532B is typically closed after the flow of dry nitrogen has had sufficient time to replace the air and moisture in chamber 512. First flow valve is then closed and the nitrogen line disconnected from the first valve. Alternatively, a single valve could be used to draw a vacuum in chamber 512 and thus purge the chamber. Purging chamber 512 substantially eliminates moisture and oxygen, which can shorten the life of QC laser diode 504. Providing at least one purge valve eliminates the need to use a purged glove box to manufacture, and subsequently, maintain illuminator 500. In connection with purging and/or filling of enclosure with dry nitrogen, illuminator 500 may include an oxygen sensor 536, pressure sensor 540 and moisture sensor 544, which may be electrically coupled to one or more corresponding readouts 548. Readout(s) 548 may be part of illuminator 500 or may, e.g., be part of bench or portable equipment (not shown) used to support the purging of chamber 512.

Illuminator 500 also comprises a power supply 552 for powering QC laser diode 504. Power supply 552 can be any power supply that provides the electrical characteristics required to operate QC laser diode 504 properly. In the case of wherein QC laser diode is pulsed, power supply 552 may further include a pulsed laser driver 556. For example, power supply model no. DLD-100B available from Directed Energy, Inc., Fort Collins, Colo., or a similar power supply may be used for power supply 552. When power supply 552 includes pulsed driver 556, it may be configured to accept a transistor-transistor logic (TTL) signal and produce an output signal that duplicates the input TTL frequency and pulse width but supplies more current as controlled by an externally supplied voltage. In one embodiment, the TTL input that drives pulsed driver 556 may be synchronized with a lock-in amplifier (not shown) employed in the receiver of the detector, e.g., receiver of FIG. 2. Such TTL-level synchronization provides a means for reducing noise, thereby increasing the practical signal-to-noise ratio and sensitivity of the system.

Illuminator 500 may further comprise a temperature sensor 560 for monitoring the temperature of QC laser diode 504, a cooler 564 to affect the temperature of the laser diode and a temperature controller 568 to control the temperature of the laser diode. Temperature sensor 560 monitors the temperature of QC laser diode 504 and provides feedback to temperature controller 568. Temperature sensor 560, e.g., may be a diode-based sensor, such a CY7 series sensor available from Omega Engineering, Inc., Stamford, Conn., or similar sensor. In alternative embodiments, temperature sensor 560 may be a thermistor or thermocouple, among other alternatives.

Cooler 564 may be implemented using, e.g., a Stirling-cycle refrigerator, a Gifford-McMahon refrigerator, a pulse-tube refrigerator, or a thermoelectric cooler. Use of a thermoelectric cooler for cooler 564 can offer advantages under certain conditions because they are generally inexpensive, efficient, reliable and have no moving parts. However, if cooler temperatures than can be provided by a thermoelectric cooler are needed, a pulsed-tube refrigerator may be a good choice for cooler 564. Cooler 564 should be placed in good thermal communication with the heat sink (not shown) of QC laser diode 504, e.g., either directly or using an intermediate thermally conductive material, such as thermal grease between the cooler and diode heat sink.

Figure 6:
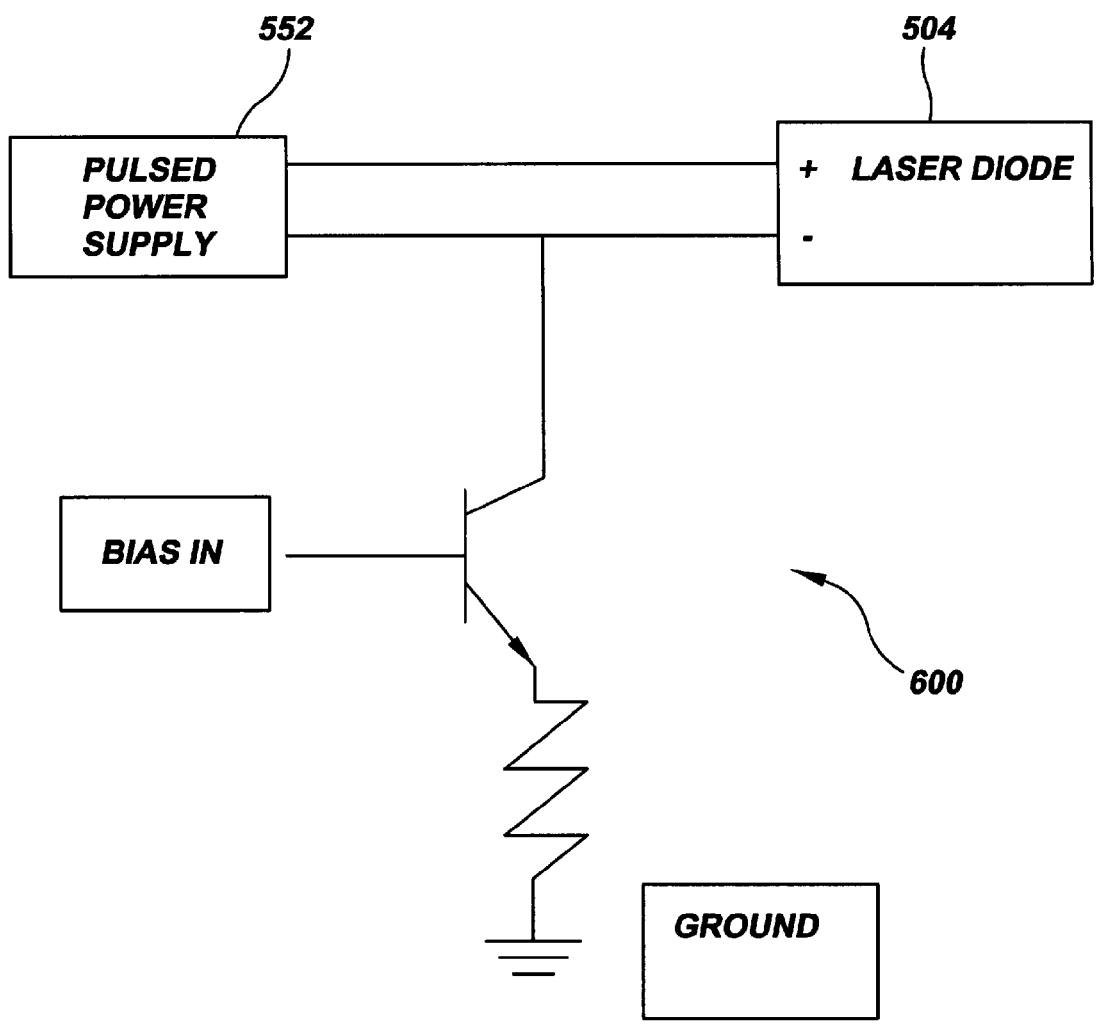
FIG. 6 is a schematic diagram of a bias tee that may be used for tuning the output of the QC laser diode of FIG. 5.
Figure 7A:
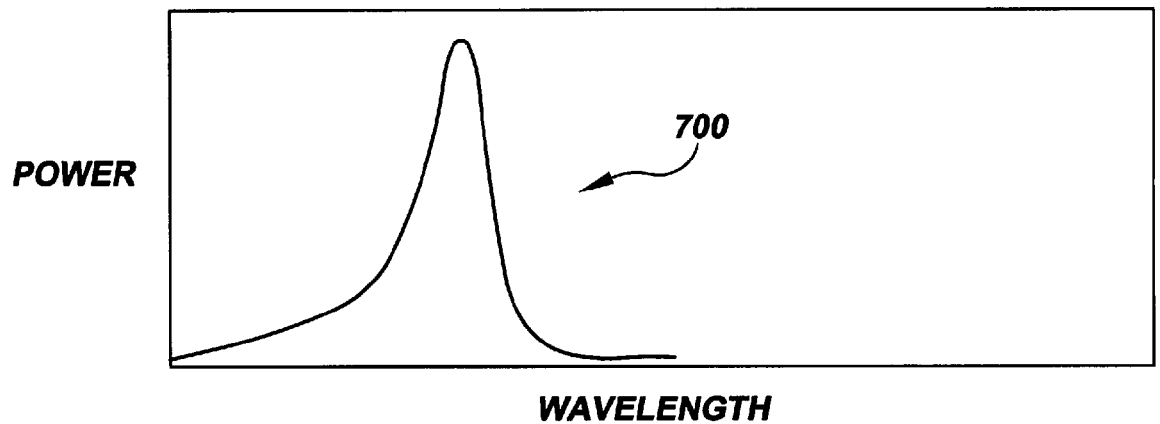
FIGS. 7A and 7B are plots of output power of the QC laser diode of FIG. 5 illustrating the wavelength shift in the output beam of the diode using the bias tee circuit of FIG. 6 for, respectively, an unbiased condition and a DC-bias condition.
Figure 7B:
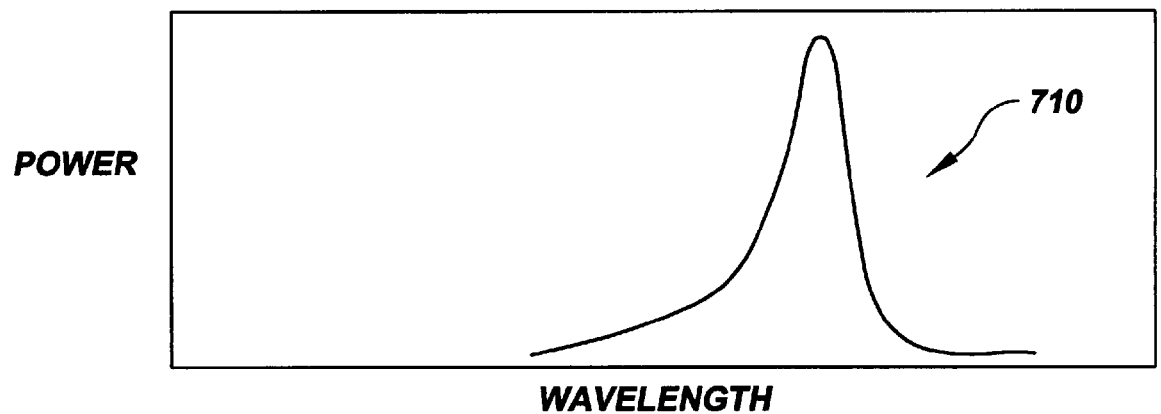
Figure 7C:
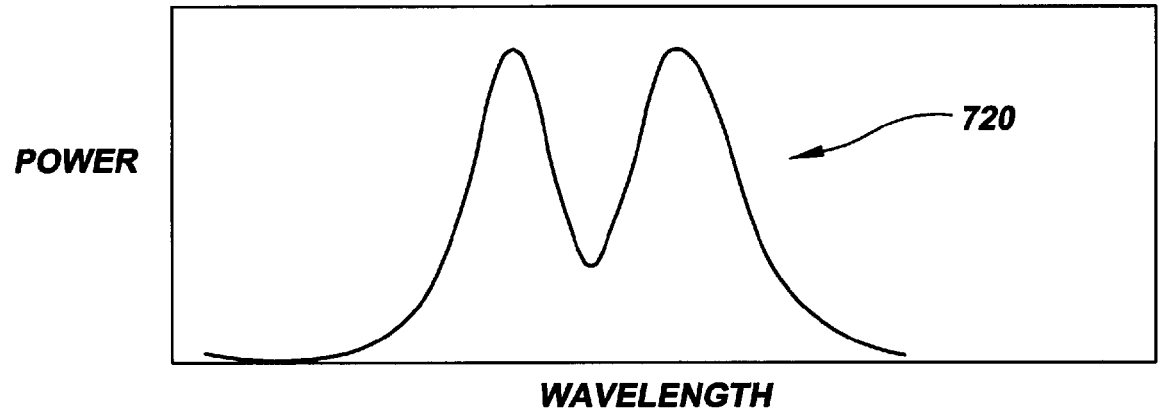
FIG. 7C is a plot of output power of the QC laser diode of FIG. 5 illustrating the wavelength shift in the output beam of the diode using the bias tee circuit of FIG. 6 for an AC-bias condition.

The output of QC laser diode 504 may be monitored, e.g., from a beam 572 emitted from the back face of the laser diode using a detector 576, such as a mercury cadmium telluride detector, a QWIP, a pyroelectric detector or a microbolometer, photoconductor, among others. Output beam 520 of QC laser diode 504 may be tuned by altering the operating temperature of the laser diode using temperature controller 568 and cooler 564 and monitoring the laser output using detector 576, which may be in communication with a detector readout 580. Alternatively, illuminator 500 may further include a bias tee, e.g., bias tee 600 of FIG. 6 located between power supply 552 and QC laser diode 504, that can be used to tune the wavelength of output beam 520. Bias tee 600 also exploits thermal effects of QC laser diode 504 to shift the operating wavelength of the laser diode. Typically, with a bias frequency of 100 Hz, the optical output frequency/wavelength shift of QC laser diode 504 is on the order of 0.1%. As the DC bias voltage is increased, it will shift the output wavelengths of QC laser diode 504 as shown in plot 700 of FIG. 7A. FIG. 7B shows a plot 710 of the output wavelengths of QC laser diode 504 without the DC bias. Alternatively, an AC bias voltage may be applied to the bias tee 600. The AC bias can be a square wave, a sine wave or other wave form. Applying an AC bias can produce bimodal wavelength output as shown in plot 720 of FIG. 7C. The frequencies/wavelengths of output beam 520 and their relative strengths can be varied by applying different waveforms, different duty cycles and/or different amplitudes using bias tee 600. For broader spectral coverage, single QC laser diode 504 can be replaced by an array of lasers designed to operate at different wavelength ranges.

Referring again to FIG. 5, illuminator 500 may optionally further comprise an optical isolator 584 to isolate QC laser diode 504 from reflected light that can interfere with the stability of output beam 520, thereby causing relative intensity noise (RIN). Optical isolator 584 may include a quarter-wave plate (QWP) retarder placed between crossed polarizers. Unfortunately, a QWP retarder is only a retarder for a single wavelength and is generally not amenable to a tunable system. An alternative embodiment of optical isolator 584 may employ a faraday rotator instead of a QWP retarder. The faraday rotator may be thought of as a variable QWP retarder. In another alternative embodiment, optical isolator 584 may include an acousto-optic cell, which imparts a frequency shift to the light equal to the frequency applied to the acousto-optic cell. Light reflected back through the cell receives a second additional frequency shift, which can be sufficient to prevent undesirable interaction with QC laser diode 504.

Although not shown in FIG. 5, illuminator 500 may further comprise one or more beam directors for directing output beam 520 of QC laser diode 504 to the region containing matter to be analyzed to determine the presence and/or identity of one or more analytes of interest. By way of illustration and not limitation, each beam director may include any one or more of a lens, beam splitter, diffraction grating, prism, diffracting element, refracting element, mirror, etc. In one embodiment, the beam director may be a parabolic mirror, which is selected because it is achromatic and, therefore, insensitive to changes in the operating wavelength of QC laser diode 504. In addition, gold or protected silver mirrors have high transmissive rates compared to lenses at mid- and far-infrared wavelengths. In addition, the beam director may be a deformable mirror or micro-electromechanical system (MEMS) device.

A sensor of the present invention, e.g., sensor 200 of FIG. 2, may be embodied in any of a number of configurations, depending upon the application. Basic configurations include a "transmissive" configuration (FIGS. 8A-8D), and "reflective" configuration (FIG. 9) and a "back-scattering" configuration (also FIG. 9). Generally, the transmissive configuration includes an illuminator that directs spectral energy through a sample region to a receiver. The transmissive configuration is useful, e.g., for security portal applications such as vehicle checkpoints and baggage and passenger screening, among others. The reflective configuration includes an illuminator that directs spectral energy to a sample present on a surface and a receiver that detects the spectral energy reflected from the sample region and surface. The reflective configuration is useful, e.g., for detecting analytes from airborne platforms, such as unmanned areal vehicles or for personnel screening and cargo searches, among others. Other uses for the reflective configuration include food safety inspection, medical diagnostics and checking surfaces for explosive residue, among many others. The back-scattering configuration includes a transmitter that directs spectral energy into a sample region and a receiver that detects the portion of the spectral energy that is back-scattered from the region. The backscattering configuration is useful, e.g., for long range detection of aerosolized vapors and particles.

Figure 8A:
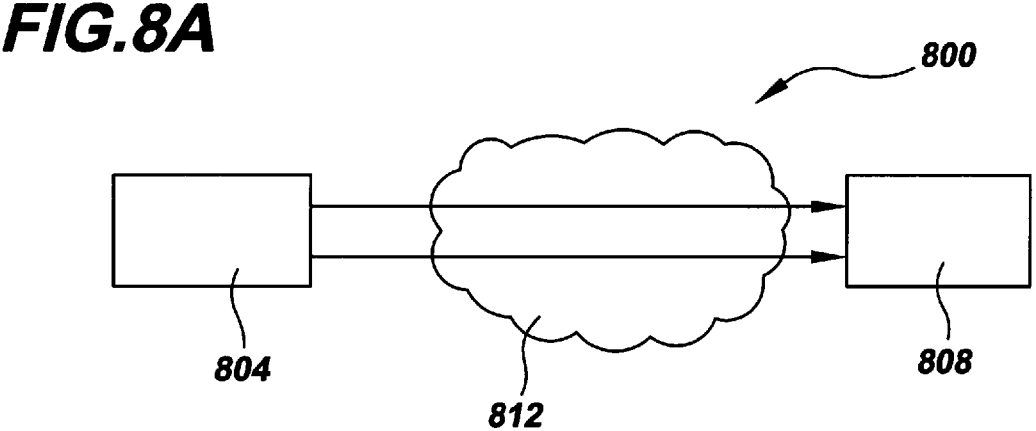
FIG. 8A is a high-level schematic diagram of a basic transmissive configuration of an analyte sensor of the present invention.

As mentioned, FIGS. 8A-8D are directed to transmissive configurations in which spectral energy that has passed through a sample region is detected and analyzed. In FIG. 8A, a transmissive configuration 800 is shown having an illuminator 804 and a receiver 808 located on opposite sides of sample region 812. Transmissive configuration 800 is the simplest transmissive configuration.

Figure 8B:
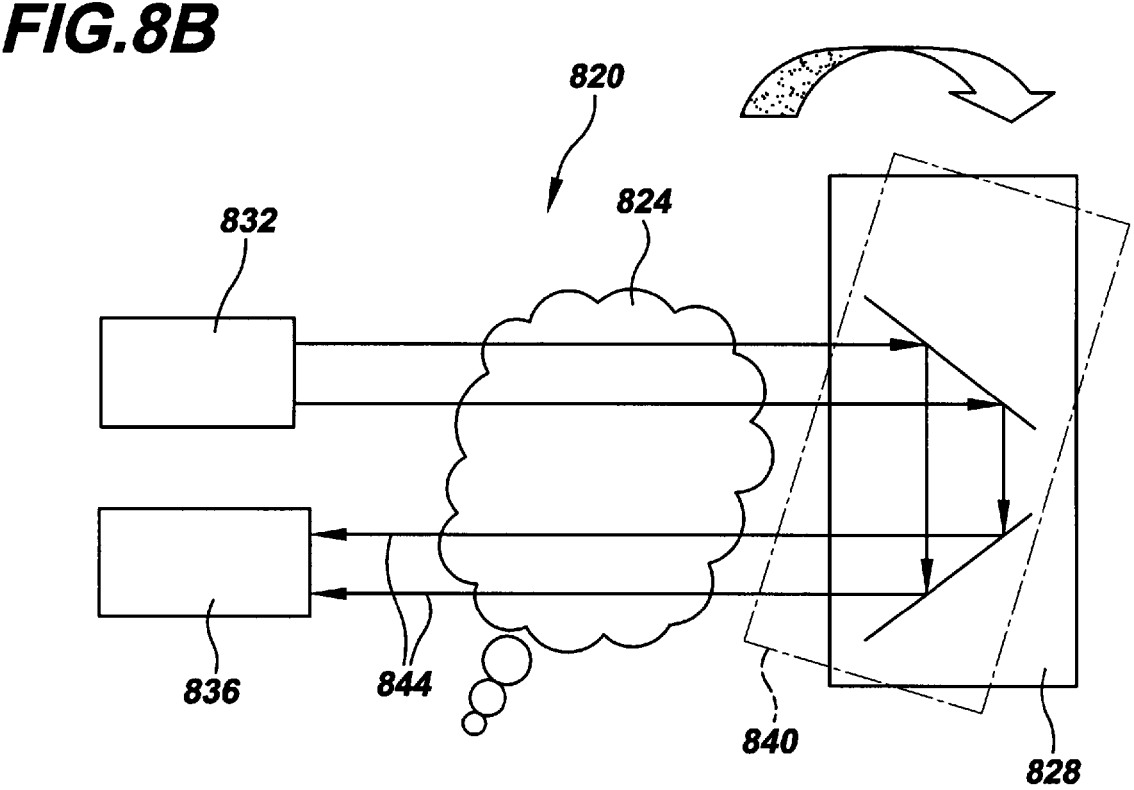
FIG. 8B is a high-level schematic diagram of a multi-pass transmissive configuration of an analyte sensor of the present invention that is insensitive to rotation.

FIG. 8B illustrates a transmissive configuration 820 having several improvements over transmissive configuration 800 of FIG. 8A. First, transmissive configuration 820 of FIG. 8B provides two passes through sample region 824 by virtue of a reflector 828, thereby doubling the sensitivity of this configuration over configuration 800 of FIG. 8A. Second, because illuminator 832 and receiver 836 of FIG. 8B are on the same side of sample region 824, they can be rigidly fixed together to reduce sensitivity of transmissive configuration 820 to vibration. Third, this arrangement can simplify alignment. In a preferred embodiment, reflector 828 may be a lateral transfer hollow retroreflector (LTHR), such as the LTHR described in U.S. Pat. Nos. 5,025,514 and 5,361,171, both of which are incorporated herein in their entireties by reference. Generally, an LTHR is an angular invariant reflector that displaces light beams laterally and reflects it back at exactly 180° opposite its angle of incidence. This lateral displacement enables illuminator 832 to be rigidly fixed side-by-side with receiver 836. Furthermore, if the LTHR is rotationally displaced (as indicated in phantom view by numeral 840), e.g., due to vibration or jarring, the displacement does not affect the angle of the return beam 844, thereby reducing the sensitivity of configuration 820 to environmental influences and simplifying alignment. As an alternative to an LTHR a simple retroreflector such as a hollow corner cube may be used.

Figure 8C:
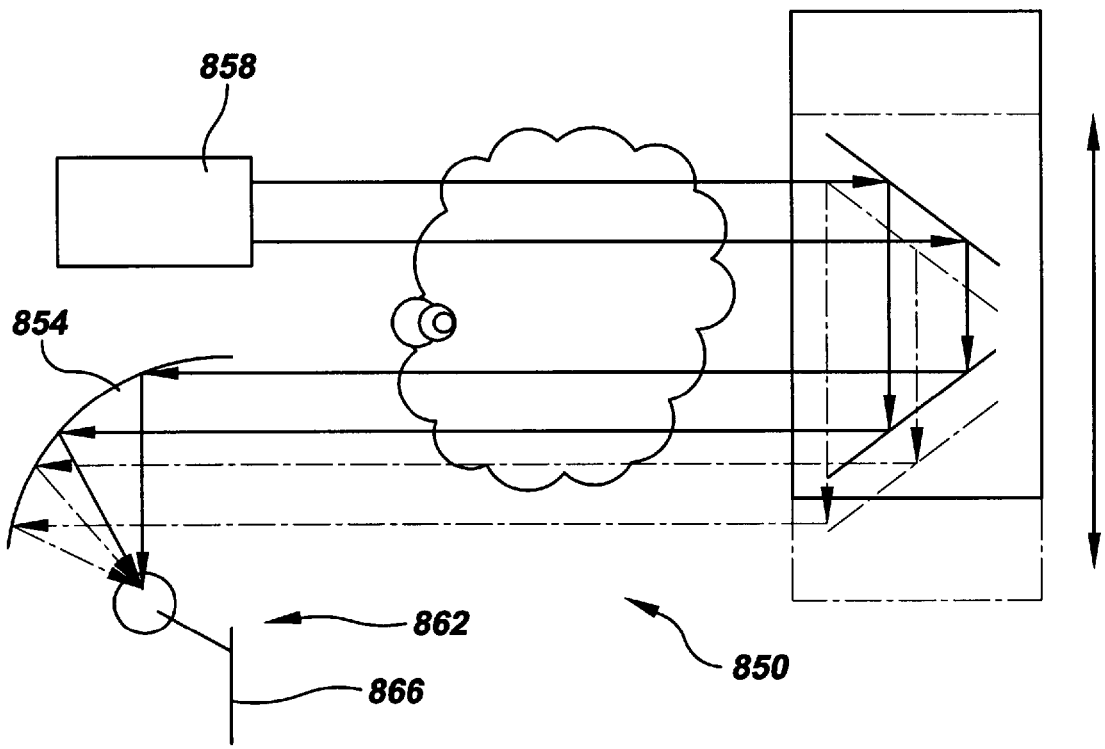
FIG. 8C is a high-level schematic diagram of another multi-pass transmissive configuration of an analyte sensor of the present invention that is insensitive to rotation and translation.

As seen in FIG. 8C, in a preferred embodiment, a transmissive configuration 850 may further include a parabolic reflector 854, such as an off-axis parabolic reflector. Since the light returning from an LTHR is guaranteed to be parallel to the light leaving illuminator 858, and since the illuminator and receiver 862 can be rigidly fixed together, transmissive configuration 850 having parabolic reflector 854 with the detector 866 of the receiver 862 placed at the focus of the parabolic reflector will be insensitive to lateral translation. Consequently, transmissive configuration 850 will be generally insensitive to rotational and translational movements within the configuration. Because of this dual insensitivity, transmissive configuration 850 is particularly well-suited to environments wherein such movement can be expected, e.g., at vehicle checkpoints for explosives or other analyte(s) at which movement of vehicles can cause vibration in the adjacent structures and equipment.

Figure 8D:
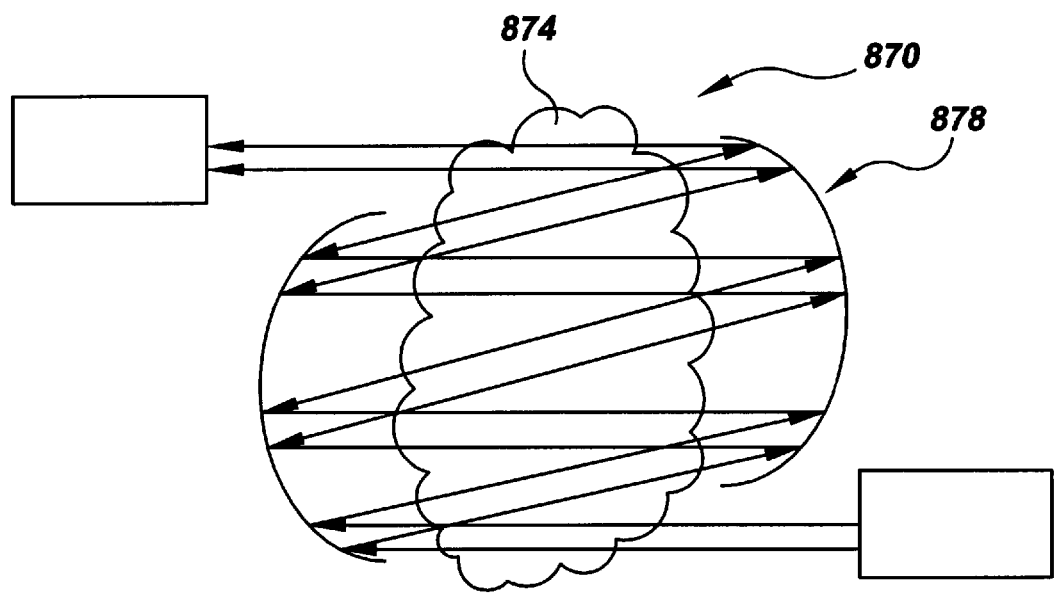
FIG. 8D is a high-level schematic diagram of a multi-pass transmissive configuration of an analyte sensor of the present invention that includes an unstable resonator.

FIG. 8D shows yet another transmissive configuration 870 in which the sample region 874 is located within the cavity of an unstable resonator 878 that provides a large number of passes through the sample region. Transmissive configuration 870 can further increase the sensitivity by providing a relatively large number of passes for the spectral energy through sample region 874.

Figure 9:
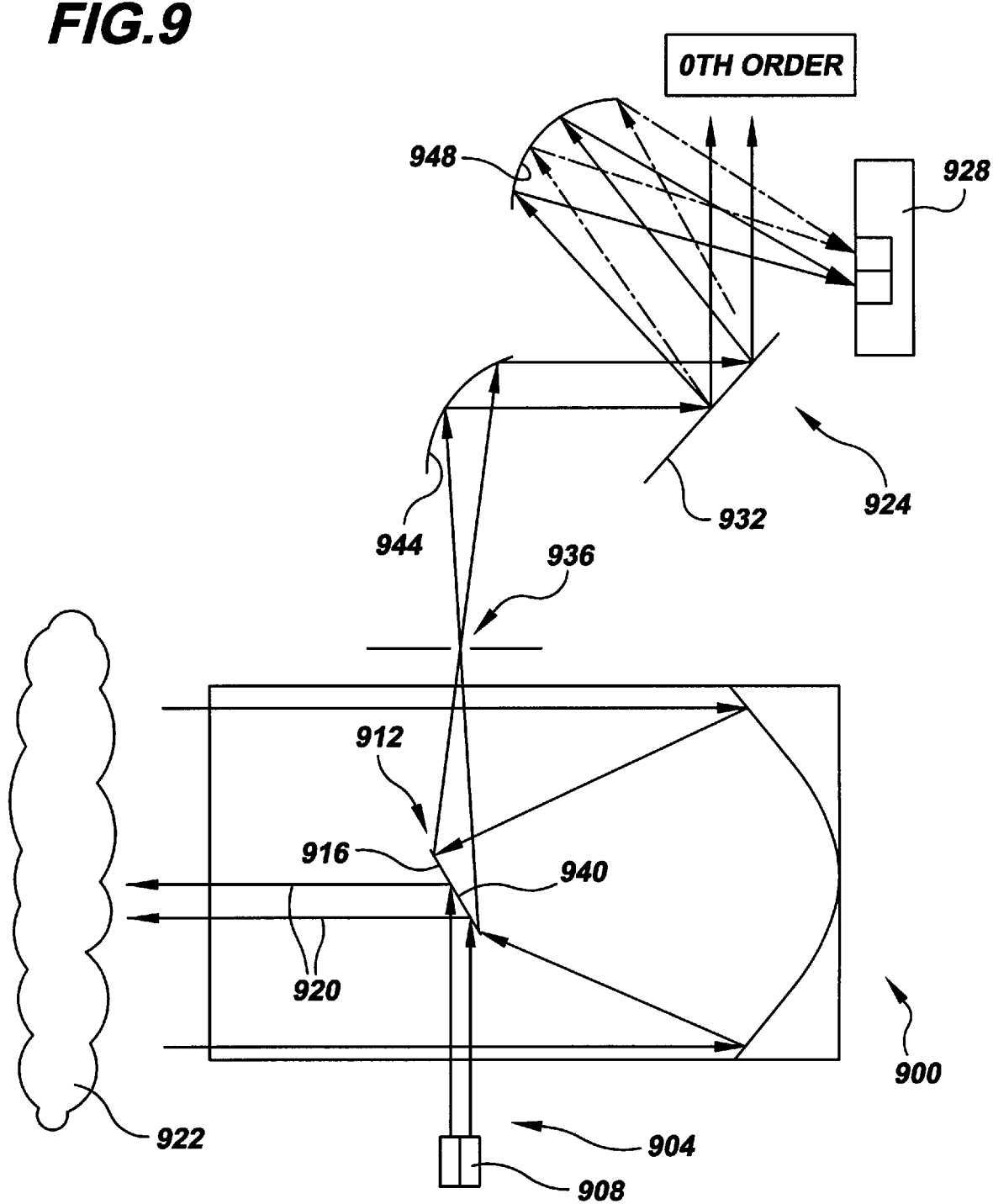
FIG. 9 is a schematic diagram of an analyte sensor of the present invention suitable for use in either a reflective configuration or a back-scatter configuration.

FIG. 9 illustrates a detector 900 of the present invention that may be considered both a reflective configuration and a back-scatter configuration. Generally, the difference is in the character of the sample region 922. In a reflective mode, the sample region is at a surface of an object such as the ground, a wall, etc. In a back-scatter mode, the sample region is generally in free space. Detector 900 may comprise an illuminator 904 having a laser array 908 and a beam director 912 that includes a mirror 916 for directing a beam 920 of spectral energy emitted by the laser array so as to direct it toward sample region 922. In this case, mirror 916 reflects beam 90°. Detector 900 may also comprise a receiver 924 that includes a broadband sensor 928 and an optional diffraction grating 932 that separates the incoming spectral energy, e.g., the portion of spectral energy emitted by laser array 908 that is reflected or back-scatter from the sample region. Diffraction grating 932 is not necessary for proper operation if a linear variable interference filter is used on the detector array. However, diffraction grating 932 can improve the signal to noise of the system by concentrating the spectral bands on the appropriate pixel. To accommodate the specific locations of illuminator 904 and receiver 924 relative to each other, detector 900 may include an aperture 936 and/or a number of mirrors, e.g., mirrors 940, 944, 948 or other optical elements/devices that create the light path(s) needed to direct that portion of incoming spectral energy to sensor array 928 needed to perform the analysis desired.

Figure 10:
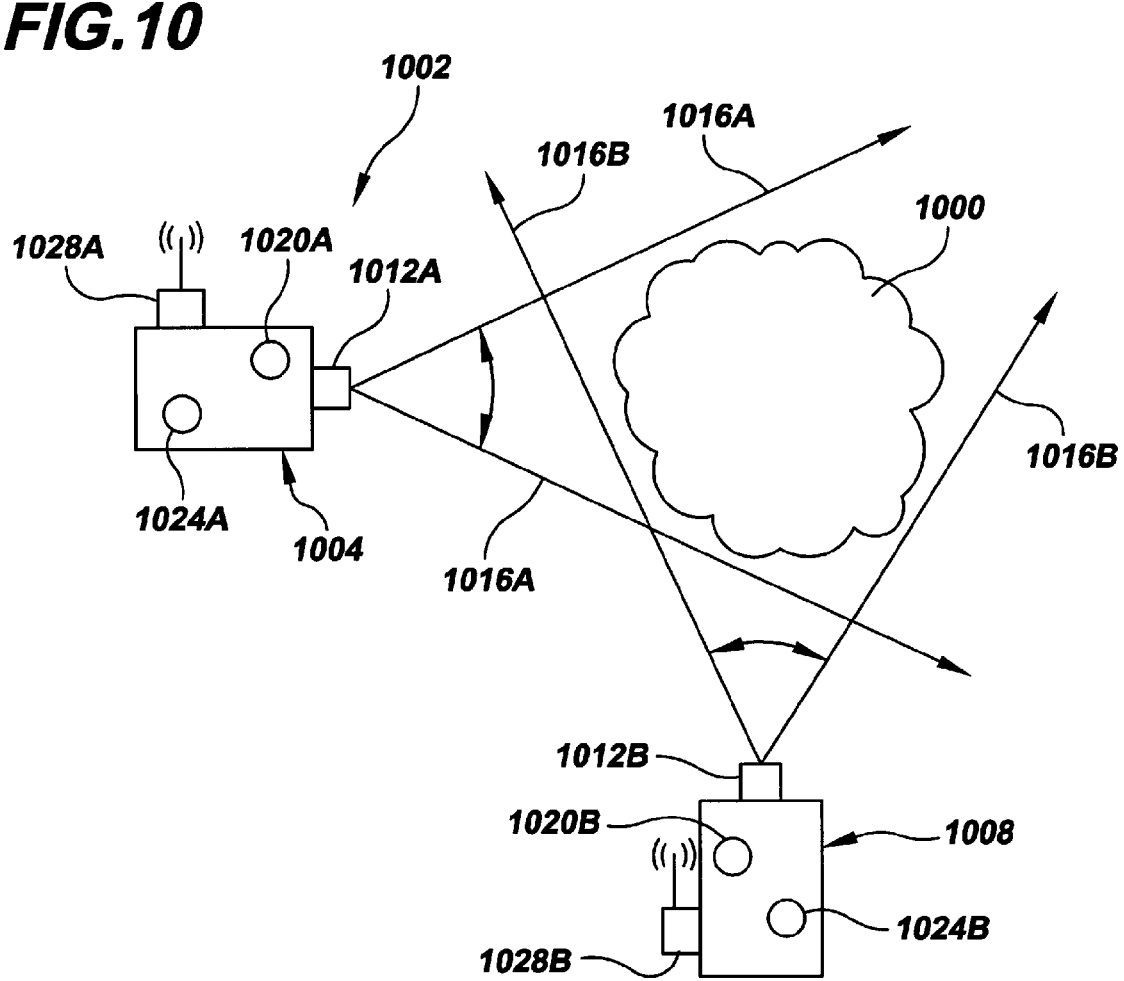
FIG. 10 is a high-level schematic diagram of a mapping system of the present invention for mapping aerosolized particles in free space.

As mentioned above, one of the uses of the present invention is to map analytes that have been detected and identified, in particular analytes that exist as aerosolized particles in a mapping region 1000 in free space. An example of a mapping system 1002 that can perform this mapping feature for aerosolized particles is shown in FIG. 10. Mapping system 1002 may include two or more ranging devices 1004, 1008, each of which may be a sensor of the present invention, such as two sensors 900 of FIG. 9. When two ranging devices 1004, 1008 are provided, they may be arranged in substantially orthogonal, or other, relation with each other and may include scanners 1012A, 1012B for scanning output beams 1016A, 1016B across mapping region and focusing back-scattered energy to the ranging devices. Scanners 1012A, 1012B are preferably capable of providing digital information regarding the angle of the beams relative to the corresponding devices for use in mapping. In the arrangement shown, ranging device 1004 may be used to scan in an arcuate fashion in a primarily longitudinal direction, while ranging device 1008 may be used to likewise scan in a primarily latitudinal direction. Other scanning approaches include the use of MEMS devices or acousto-optic deflectors. Range information can be provided, e.g., if a counter is used to measure the time between outgoing and incoming pulses. Range resolution is limited by the response speed of the detector, amplifier and digitization electronics.

Scanners 1012A, 1012B cause beams 1016A, 1016B to sweep the direction of the spectral energy beam and permit ranging devices 1004, 1008 to collect range-resolved information, e.g., in corresponding arcs. Ranging devices 1004, 1008 may each further include a global positioning sensor 1020A, 1020B that provide global positioning information for the devices. In addition, each ranging device 1004, 1008 may be equipped with a digital compass 1024A, 1024B that provides orientation information that represents the direction that device is facing. Since the positions of both ranging devices 1004, 1008 are known, as are the directions the devices are facing, the relative angles of beams 1016A, 1016B and range-resolved data at any given time, it is possible to combine the data from both devices using triangulation methods. Thusly cooperating ranging devices 1004, 1008 and other components can be used to provide maps of aerosolized particles, as well as their identity, position, concentration, velocity, particle size and direction of travel.

Further, each ranging device 1004, 1008 may optionally be equipped with a communications device 1028A, 1028B, e.g., a transmitter or transceiver, that allows the acquired data to be transmitted to other cooperating devices or to a remote destination, such as a host computer system (not shown). Communications devices 1028A, 1028B may be equipped to transmit data securely via a communications link, such as a cellular link, a radio-frequency link, a microwave link, a free-space optical link or a satellite link, among others. These, or one or more other, communications devices may be used to communicate the map(s) generated by mapping system to, e.g., personnel in the field in near real time. Preferably said communications will encrypt data transmitted.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A method of identifying a biological classification of virus present in a sample, the method comprising:

illuminating the sample with a spectral energy band across at least a portion of the characteristic absorption band of the analyte using an illuminator consisting essentially of one or more broadband quantum cascade lasers so as to provide the spectral energy band across a broadband of wavelengths;

collecting spectral data regarding the sample using a detector; and determining a biological classification of the virus as a function of the spectral data;

wherein the spectral data comprises a plurality of spectral data points and said collecting includes collecting the spectral data points simultaneously with one another; and wherein said illuminating comprises illuminating the sample using a Fabry-Perot quantum cascade laser.

2. A method according to claim 1, wherein said determining of the biological classification of the virus includes identifying a virus species.

3. A method according to claim 1, wherein the sample includes viruses of differing biological classifications, the method further comprising performing a multivariate analysis of the spectral data so as to distinguish between the differing biological classifications.

4. A method of identifying a biological classification of micro-organisms present in a sample, the method comprising:

illuminating the sample with a spectral energy band across at least a portion of the characteristic absorption band of the analyte using an illuminator consisting essentially of one or more broadband quantum cascade lasers so as to provide the spectral energy band across a broadband of wavelengths;

simultaneously collecting spectral data, from across the broadband of wavelengths, regarding the sample using a detector; and determining the biological classification of the micro-organisms as a function of the spectral data;

wherein said illuminating comprises illuminating the sample using a Fabry-Perot quantum cascade laser.

5. A method according to claim 4, wherein said determining of the biological classification of the micro-organisms includes identifying the species.

6. A method according to claim 4, wherein the sample includes micro-organisms of differing biological classifications, the method further comprising performing a multivariate analysis of the spectral data so as to distinguish between the differing biological classifications.

7. A method according to claim 4, wherein the micro-organisms include a fungus and said determining the biological classification of the micro-organisms includes determining the biological classification of the fungus.

8. A method according to claim 7, wherein said illuminating comprises illuminating the sample using a Fabry-Perot quantum cascade laser.

9. A method according to claim 7, wherein said determining of the biological classification of the fungus includes identifying a fungal species.

10. A method according to claim 7, wherein the sample include's fungi of differing biological classifications, the method further comprising performing a multivariate analysis of the spectral data so as to distinguish between the differing biological classifications.

11. A method according to claim 4, wherein ones of the micro-organisms are bacteria and said determining the biological classification of the micro-organisms includes determining the biological classification of the bacteria.

12. A method according to claim 11, wherein said illuminating comprises illuminating the sample using a Fabry-Perot quantum cascade laser.

13. A method according to claim 11, wherein said determining of the biological classification of the bacteria includes identifying the bacterial species.

14. A method according to claim 11, wherein the sample includes bacteria of differing biological classifications, the method further comprising performing a multivariate analysis of the spectral data so as to distinguish between the differing biological classifications.

15. A method, comprising:

illuminating a plurality of particles, from a stand off distance, with a spectral energy band across at least a portion of the characteristic non-absorption band of the plurality of particles using an illuminator consisting essentially of one or more broadband quantum cascade lasers so as to provide the spectral energy band across a broadband of wavelengths;

collecting spectral data regarding the plurality of particles using a detector; and determining sizes of the particles based on the spectral data;

wherein said illuminating comprises illuminating the sample using a Fabry-Perot quantum cascade laser.

16. A method according to claim 15, further comprising determining a location of the particles using the spectral data.

17. A method according to claim 15, further comprising determining a velocity of the particles using the spectral data.

\* \* \* \* \*